(12) United States Patent
Sone et al.

(10) Patent No.: US 10,683,274 B2
(45) Date of Patent: Jun. 16, 2020

(54) 3-SUBSTITUTED CARBONYL-NAPHTHO[2,3-B]FURANE DERIVATIVE OR PHARMACEUTICALLY ACCEPTABLE SALT THEREOF

(71) Applicant: Boston Biomedical, Inc., Cambridge, MA (US)

(72) Inventors: Toshihiko Sone, Osaka (JP); Wataru Hirose, Osaka (JP); Naoaki Shimada, Osaka (JP); Chiang Li, Cambridge, MA (US); Wei Li, Wayland, MA (US); David Leggett, Milton, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 0 days.

(21) Appl. No.: 16/204,730

(22) Filed: Nov. 29, 2018

(65) Prior Publication Data

US 2019/0241535 A1    Aug. 8, 2019

Related U.S. Application Data

(63) Continuation of application No. 16/005,426, filed on Jun. 11, 2018, now abandoned, which is a continuation of application No. 15/116,850, filed as application No. PCT/US2015/014865 on Feb. 6, 2015, now Pat. No. 10,017,488.

(60) Provisional application No. 61/936,925, filed on Feb. 7, 2014.

(51) Int. Cl.

| C07D 307/92 | (2006.01) |
|---|---|
| A61K 31/343 | (2006.01) |
| A61K 31/443 | (2006.01) |
| A61K 31/497 | (2006.01) |
| C07D 405/04 | (2006.01) |
| C07D 405/12 | (2006.01) |
| C07D 413/06 | (2006.01) |

(52) U.S. Cl.
CPC .......... *C07D 307/92* (2013.01); *A61K 31/343* (2013.01); *A61K 31/443* (2013.01); *A61K 31/497* (2013.01); *C07D 405/04* (2013.01); *C07D 405/12* (2013.01); *C07D 413/06* (2013.01)

(58) Field of Classification Search
CPC .......................... C07D 307/92; A61K 31/343
USPC .......................................... 549/456; 514/468
See application file for complete search history.

(56) References Cited

U.S. PATENT DOCUMENTS

| 10,017,488 | B2 | 7/2018 | Sone et al. |
| 2006/0142271 | A1 | 6/2006 | Muller et al. |
| 2009/0163545 | A1* | 6/2009 | Goldfarb ............... A61K 31/122 |
| | | | 514/312 |
| 2013/0345176 | A1 | 12/2013 | Jiang et al. |
| 2017/0174646 | A1 | 6/2017 | Sone et al. |

FOREIGN PATENT DOCUMENTS

| CN | 103002890 A | 3/2013 |
| CN | 103214506 A | 7/2013 |
| CN | 103402993 A | 11/2013 |
| EP | 3102036 A1 | 12/2016 |
| JP | 63196576 A | 8/1988 |
| JP | H06199787 A | 7/1994 |
| JP | 1121284 A | 1/1999 |
| JP | 2002517397 A | 6/2002 |
| JP | 2010539095 A | 12/2010 |
| WO | WO-9962909 A2 | 12/1999 |
| WO | WO-2004087153 A2 | 10/2004 |
| WO | WO-2006098355 A1 | 9/2006 |

(Continued)

OTHER PUBLICATIONS

Ghera et al., Tetrahedron Letters (1986), 27(33), 3935-8.*
Chuang et al., Tetrahedron (1998), 54(34), 10043-10052.*
Chuang et al., Tetrahedron (1999), 55(37), 11229-11236.*
Hu et al., Synthesis (2005), (10), 1605-1610.*
Choi et al., Journal of the Korean Chemical Society (2005), 49(5), 449-460.*
Park et al., European Journal of Pharmacology (2005), 527(1-3), 31-36.*
Stasevych et al., Chemistry of Heterocyclic Compounds (New York, NY, United States) (2008), 44(7), 897-898.*
Wang et al., Journal of Organic Chemistry (2013), 78(12), 6211-6222.*

(Continued)

*Primary Examiner* — Niloofar Rahmani
(74) *Attorney, Agent, or Firm* — Schwegman Lundberg & Woessner, P.A.

(57) ABSTRACT

The present invention provides a compound of the following Formula (1) or a pharmaceutically acceptable salt thereof:

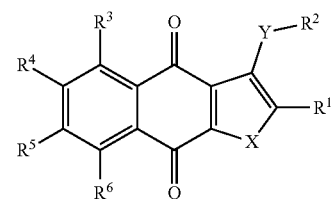

wherein X is an oxygen atom and the like; Y is —CO—, —SO$_2$— and the like; R$^1$ is an optionally-substituted C$_{1-6}$ alkyl group, an optionally-substituted C$_{1-6}$ alkylcarbonyl group and the like; R$^2$ is an optionally-substituted C$_{1-6}$ alkyl group, an optionally-substituted C$_{1-6}$ alkoxy group, an optionally-substituted amino group, an optionally-substituted 5- to 12-membered monocyclic or polycyclic saturated heterocyclic group and the like; R$^3$, R$^4$, R$^5$, and R$^6$ are independently a hydrogen atom and the like which exhibits excellent effects in suppressing the proliferation and sphere-forming ability of cancer cells, and can be useful as an antitumor drug or cell growth inhibitor.

1 Claim, No Drawings

(56) References Cited

FOREIGN PATENT DOCUMENTS

| WO | 2009036059 | * | 3/2009 |
|---|---|---|---|
| WO | WO-2011116398 A1 | | 9/2011 |
| WO | WO-2011116399 A1 | | 9/2011 |
| WO | WO-2012119265 A1 | | 9/2012 |
| WO | WO-2015120304 A1 | | 8/2015 |

OTHER PUBLICATIONS

Sun et al., Journal of Organic Chemistry (2013), 78(20), 10560-10566.*

U.S. Appl. No. 15/116,850, filing date Aug. 5, 2016, 3-Substituted Carbon'S L-Naphtho[2,3-B]Furane Derivative or Pharmaceutically Acceptable Salt Thereof.

U.S. Pat. No. 10,017,488 filing date Aug. 5, 2016, 3-Substituted Carbon'S L-Naphtho[2,3-B]Furane Derivative or Pharmaceutically Acceptable Salt Thereof.

U.S. Appl. No. 16/005,426 filed Jun. 11, 2018, 3-Substituted Carbonyl-Naphtho[2,3-B]Furane Derivative or Pharmaceutically Acceptable Salt Thereof.

"U.S. Appl. 15/116,850, Non Final Office Action dated Apr. 11, 2017", 32 pgs.

"U.S. Appl. No. 15/116,850, Notice of Allowance dated Mar. 9, 2018", 5 pgs.

"U.S. Appl. No. 15/116,850, Notice of Allowance dated Aug. 17, 2017", 8 pgs.

"U.S. Appl. No. 15/116,850, Notice of Allowance dated Nov. 29, 2017", 5 pgs.

"U.S. Appl. No. 15/116,850, Preliminary Amendment filed Aug. 5, 2016", 73 pgs.

"U.S. Appl. No. 15/116,850, Response filed Aug. 7, 2017 to Non Final Office Action dated Apr. 11, 2017", 16 pgs.

"Chinese Application Serial No. 201580007175.8, Office Action dated Feb. 8, 2018", w/ English Translation, 20 pgs.

"Chinese Application Serial No. 201580007175.8, Office Action dated Oct. 18, 2018", (w/English Translation), 5 pages.

"Chinese Application Serial No. 201580007175.8, Response filed Jun. 22, 2018 to Office Action dated Feb. 8, 2018", w/ English Claims, 21 pgs.

"European Application Serial No. 15746714.3, Communication Pursuant to Article 94(3) EPC dated Dec. 14, 2018", 4 pgs.

"European Application Serial No. 15746714.3, Extended European Search Report dated Aug. 18 2017", 14 pgs.

"European Application Serial No. 15746714.3, Response filed Mar. 23, 2017 to Communication pursuant to Rules 161(1) and 162 EPC dated Sep. 23, 2016", 11 pgs.

"European Application Serial No. 15746714.3, Response filed Jun. 22, 2018 to Extended European Search Report dated Aug. 18, 2017", 17 pgs.

"International Application Serial No. PCT/U52015/014865, International Preliminary Report on Patentability dated Aug. 18, 2016", 6 pgs.

"International Application Serial No. PCT/US2015/014865, International Search Report dated Apr. 21, 2015", 3 pgs.

"International Application Serial No. PCT/US2015/014865, Written Opinion dated Apr. 21, 2015", 4 pgs.

"Japanese Application Serial No. 2016-548371, Examiners Decision of Final Refusal dated Apr. 1, 2019", (w/English Translation), 7 pages.

"Japanese Application Serial No. 2016-548371, Office Action dated Sep. 18, 2018", w/ English Translation, 13 pgs.

"Japanese Application Serial No. 2016-548371, Office Action dated Sep. 26, 2019", w/ English Translation, 6 pgs.

"Japanese Application Serial No. 2016-548371, Response filed Jul. 25, 2019 to Examiners Decision of Final Refusal dated Apr. 1, 2019", w/English Claims, 23 pgs.

"Japanese Application Serial No. 2016-548371, Response Filed Dec. 4, 2018 to Office Action dated Sep. 18, 2018", (w/English Claims), 24 pages.

"PubChem Substance summary for CID 11002488 Deposit", (Oct. 16, 2006), 8 pgs.

"PubChem Substance summary for CID 4493092 Deposit", (Sep. 15, 2005), 10 pgs.

Al-Hajj, M., et al., "Self-Renewal and Solid Tumor Stem Cells", Oncogene, 23, (2004), 7274-7282.

Boman, Bruce M, "Cancer Stem Cells: A Step Toward the Cure", Journal of Clinical Oncology, vol. 26, No. 17, (2008), 2795-2799.

Choi, "Correlation between the binding mode and inhibitory activity of benz[f]indole-4,9,dione analogs with human topoisomerase I-DNA", [Online] Retrieved from the Internet : <http://ocean.kisti.re.kr/downfile/volume/chemical/JCGMDC/2005/v49n5/JCGMDC_2005_v49n5_449.p. d>, (1 Jan 2005), 12 pages.

Chuang, Che-Ping, "Manganese (IH) Acetate Initiated Oxidative Free Radical React", Tetrahedron 55 C1999), 11229-11236.

Diaz, et al., "Furanonaphthoquinones from Tabebuia ochracea ssp. neochrysanta", J. Nat. Prod. 59, (1996), 423-424.

Hirai, et al., "Furanonaphthoquinone Analogs Possessing Preferential Antitumor Activity Compared to Normal Cells", Cancer Detection and Prevention. 23.6, (1999), 539-550.

Hisahiro, Hagiwara, et al., "Domino Michael O alkylation reaction one pot synthesis of 2 4 diacylhydrofuran derivatives and its application to antitumor naphthofuran synthesis", J. Chem. Soo Perkin Trans 1, (2001), 2946-2957.

Hisahiro, Hagiwara, et al,, "Tandem nucleophilic reaction leading to hydrofurans application to one pot synthesis of antitumor naphthofuran natural product", Heterocycles vol. 51 No. 3, (1999), 4 pages.

Hu, Hua-You, et al., "A Direct One-Pot Synsthesis of Naphtho[2,3-b]furan-4,9-dione Derivatives via C, O-Diaikylation of B-Dicarbonyl Compounds by 2,3-Dichloro-I, 4-naphtho-quinones", Department of Chemistry Nunjing University, (2005), 1605-1610.

Hua-You, Hu, et al., "Direct One-pot synthesis of naphtho[2,3-b]furan-4,9-dione Derivatives via C,O-Dialkylation of [beta]Dicarbonyl Compounds by 2,3-Dichloro-1,4-naphthoquinones", Synthesis, No. 10, (Jan. 1, 2005), 1605-1610.

Kenneth, O Eyong, et al., "Semisynthesis and antitumoral activity of 2-acetylfuranonaphthoquinone and other naphthoquinone derivatives from lapachol", Bioorganic & Medicinal Chemistry Letters, (2008), 5387-5390.

Kobayashi, et al,, "One-Pot Synthesis of Naphtho[2,3-b]furan-4,9-diones by Sequential Coupling/Ring Closure Reactions", Tetrahedron Letters, vol. 38, No, 5, (1997), 837-840.

Koyoma, et al., "Micellar electrokinetic chromatography (MEKC) separation of furanonaphthoquinones from Tabebuia impetiginosa", Chem. Pharm, Bull (Tokyo), 48(6), (Jun. 2000), 873-875.

Kuehne, M E, "Photochemical and thermal reactions of naphthoquinones and ynamines. Formations of intermediate cyclobutadienes", The Journal of Organic Chemistry, vol. 37, No. 25, (Dec. 1, 1972), 4031-4036.

Lee, H J, "Synthesis and Cytotoxicity Evaluation of 2-Amino- and 2-Hydroxy-3-ethoxycarbonyl-N- Substituted-benzoglindole-4, 9-dione Derivatives", Bioorg Med Chem, 11(7), (2003), 1511-9.

Lee, Hyun-Jung, et al., "Synthesis and Cytoxicity Evaluation of 2-Amino- and 2-Hydroxy-3-ethoxycarbonyl-N-substituted-benzo[f]indole-4, 9-dione Derivatives", Biorganic & Medicinal Chemistry, vol. 11, (2003), 1511-1519.

Lobo, Neethan A, et al., "The Biology of Cancer Stem Cells", The Annual Review of Cell and Developmental Biology, 23, (2007), 675-699.

Muller, Klaus, et al., "Potential Antipsoriatic Agents: Lapacho Compounds as Potent Inhibitors of HaCaT Cell Growth", J Nat Prod 62, (1999), 1134-1136.

No Author, "International Research Congress on Natural Product as Medicinal Agents", Journal of Medicinal Plant Research, vol. 39, Planta Med, (Jul. 1980).

Ogawa, et al., "Cytotoxic Activity toward KB Cells of 2-Substituted Naptho[2,3-b]furan-4,9 diones and Their Related Compounds", Bioscience Biotechnology and Biochemistry, 70.4, (2006), 1009-1012.

Park, Hyen Joo, et al., "Cytotoxicity and DNA Topoisomerase Inhibitory Activity of Benz[f]indole-4,9-dione Analogs", Bioscience, Biotechnology, and Biochemistry, vol. 67, No. 9, (2003), 1944-1949.

(56) References Cited

OTHER PUBLICATIONS

Park, Hyen Joo, et al., "Inhibitory effects of a benz[f]indole-4,9-dione analog on cancer cell metastasis mediated by the downregulation of matrix metalloproteinase expression in human HT1080 fibrosarcoma cells", European Journal of Pharmacology, vol. 527, (Dec. 19, 2005), 31-36.

Peraza-Sanchez, Sergio R, et al., "Cytotoxic Constituents of the Roots of Ekmanianthe longiflora", Journal of Natural Products, vol. 63, No. 4, (2000), 492-495.

Perez-Sacau, et al., "Synthesis and Pharrnacophore Modeling of Naphthoquinone Derivatives with Cytotoxic Activity in Human Promyelocytic Leukemia HL-60 Cell Line", J. Med. Chem. 50, (2007), 696-706.

Periera, et al., "Invasion-associated MMP-2 and MMP-9 are up-regulated intracellularly in concert with apoptosis linked to melanoma cell detachment", Clinical and Experimental Metastasis, 22, (2005), 285-295.

Ponti, et al., "Isolation and in vitro propagation of tumorigenic breast cancer cells with stem/progenitor cell properties", Cancer Res, 65(13), (2005), 5506-11.

Rao, et al., "Plant anticancer agents. Xii. isolation and structure elucidation of new cytotoxic quinones from Tabebuia cassinoides", Journal of Natural Products, 45(5), (1982), 600-604.

Rieber, et al., "Relationship of Mcl-1 isoforms, ratio p21WAF1/cyclin A, and Jun kinase phosphorylation to apoptosis in human breast carcinomas", Biochemical and Biophysical Research Communications 297, (2002), 943-949.

Shukla, G, "DMAP Mediated One-Pot Domino Thienannulation: A Versatile, Gegioselective and Green Mechanochemical Rooute to Naphtho [2,3-b]thiophenes", Electronic Supplementary Material (ESI) for RSC Advances, J Royal Soc Chem, [Online]retrieved from the internet: <https://www.rsc.org/suppdata/ra/c3/c3ra41100a/c3ra41100 a.pdf>, (Jan. 1, 2013).

Shukla, Gaurav, et al., "DMAP mediated one-pot domino thienannulation: aversatile, regioselective and green mechanochemicalroute to naphtha [2, 3-b] thiophenes", RSC Advances, vol. 3, Supporting Information, 1. 3 Experimental Data, (Jan. 1, 2013), 13811-13817.

Simamura, et al., "Furanonaphthoquinones Cause Apoptosis of Cancer Cells by Inducing the Production of Reactive Oxygen Species by the Mitochondrial Voltage-Dependent Anion Channel", Cancer Biology & Therapy 5:11, (Nov. 2006), 1523-1529.

Solorzano, et al., "Decreased glycolytic metabolism accelerates apoptosis in response to 2-acetyl furanonaphthoquinone in K1735 melanoma irrespective of bcl-2 overexpression", Cancer Bio. Ther, vol. 4, No. 3, (Mar. 2005), 329-335.

Sun, Jin-Wei, et al., "Copper(II)-Catalyzed Sequential C,N-Difunctionalization of 1,4-Naphthoquinone for the Synthesis of Benzo[ f ]indole-4,9-diones under Base-Free Condition", The Journal of Organic Chemistry, vol. 78, No. 20, (Oct. 2013), 10560-10566.

Takano, et al., "Tumor-specific cytotoxicity and type of cell death induced by naphtho[2,3-b]furan-4,9-diones and related compounds in human tumor cell lines: relationship to electronic structure", Anticancer Research, 29, (2009), 455-464.

Tseng, C C, et al., "Cerium Salts in the Oxidative Free Radical Reactions Between 2-Amino-1,4-Naphthoquinones and 13-dicarbonyl Compounds", Tetrahedron, 58(38), 7625-33.

Tseng, C-M, et al., "Solvent Effects on the Oxidative Free Radical Reactions of 2-Amino-1,4-Naphthoquiones", Tetrahedron, 60(52), (Dec. 20, 2004), 12249-60.

Wang, Wei, et al., "Photoinduced Reactions of para -Quinones with Bicyclopropylidene Leading to Diverse Polycyclic Compounds with Spirocyclopropanes", The Journal of Organic Chemistry, vol. 78, No. 12, (Jun. 21, 2013), 6211-6222.

Wu, Y L, et al., "Oxidative Free Radical Reactions between 2-Amino-1,4-Naphthoquinones and Carbonyl Compounds", Tetrahedron, 57(26), 5543-9.

Yi, H-W, "A Simple Synthesis of 4-Chloro-5-hydroxy-1 H-benzo[g]indoles", J Heterocycl Chem, 42(1), (Jan. 1, 2005), 147-51.

Yi, Hyung-Woo, et al,, "A Simple Synthesis of 4-Chloro-5-hydroxy-IH-benzo[g]indoles", Journal of Heterocyclic Chemistry, vol. 42, (2005), 147-151.

Yong, Rok Lee, et al., "Ceric Ammonium Nitrate (CAN)-Mediated Oxidative Cycloaddition of 1,3-Dicarbonyls to Conjugated Compounds, Efficient Synthesis of Dihydrofurans, Dihydrofurocournarins, Dihydrofuroquinolinones, Dihydrofurophenalenones, and Furonaphthoquinone Natural Products", Tetrahedron 56, (2000), 8845-8853.

\* cited by examiner

3-SUBSTITUTED CARBONYL-NAPHTHO[2,3-B]FURANE DERIVATIVE OR PHARMACEUTICALLY ACCEPTABLE SALT THEREOF

TECHNICAL FIELD

The present invention relates to a 3-substituted carbonyl-naphtho[2,3-b]furane derivative or pharmaceutically acceptable salt thereof which is useful as a medicament. In detail, the present invention relates to a pharmaceutical composition comprising the 3-substituted carbonyl-naphtho[2,3-b]furane derivative or pharmaceutically acceptable salt thereof. The present invention also relates to a medicament comprising the 3-substituted carbonyl-naphtho[2,3-b]furane derivative or pharmaceutically acceptable salt thereof.

BACKGROUND ART

Cancer is caused by the genetic abnormality due to radiation, ultraviolet, carcinogen, virus, and the like. The number of deaths due to cancer is increasing yearly, and currently cancer is the top cause of death in Japan. The means for treating such cancer include, for example, an antitumor drug, a surgery, a radiation therapy, and an immunotherapy, in which the therapy with an antitumor drug is the most important as a medical therapy. Major antitumor drugs act on any of a metabolism of nucleic acid precursor, a DNA synthesis, an RNA synthesis and a protein synthesis. However, such metabolic process is done not only in a cancer cell, but also in a normal cell. Thus, many antitumor drugs act on a cancer cell as well as a normal cell, and the action on a normal cell causes various side-effects.

Recently, a molecular target drug which is a new type of antitumor drugs is used. The molecular target drug is a drug designed to target a molecular which is specifically expressed in each cancer. Accordingly, it is thought that a molecular target drug is more specific for cancer compared with conventional antitumor drugs, and has low side-effects. A molecular target drug, however, has other problems that new side-effects happen and the choice of drugs is restricted, though hitherto-known side-effects are reduced. The above-mentioned antitumor drugs have been clinically used for treating cancer or life-sustaining a patient suffering from cancer, but the drugs have many unresolved problems including the above-mentioned side-effects. Thus, the development of a new anti-cancer drug is a still important challenge.

The research in recent years has clarified that a cancer stem cell (CSC) having self-renewal capacity exists, which is closely related to the malignant progression of cancer. Each CSC for almost all human major cancers such as breast cancer, colon cancer, lung cancer, and hematologic malignancy has been already identified (Non-Patent Reference 1). The biological property of a CSC is very different from that of a normal cancer cell differentiated from a CSC. It shows that a CSC plays a large role in the continuing proliferation of malignant tumor, the metastasis of cancer, the relapse and the resistance for an antitumor drug. The conventional therapy which targets a normal cancer cell constituting a large part of tumor mass is expected to reduce the size of tumor, but not expected to bring in a meaningful survival effect unless also targeting CSC simultaneously. Thus, it is very prospective to target a CSC to seek a new therapy for cancer (Non-Patent Reference 2). One of the properties of a CSC is to have self-renewal capacity (Non-Patent Reference 3). A reliable method established as a method of evaluating the cell self-renewal capacity is a measurement of the sphere-forming ability of cancer cells, which is done under non-adherent state in the absence of serum (Non-Patent Reference 4). A compound inhibiting the growth of cancer cells which are non-CSCs and suppressing the sphere-forming ability of cancer cells can be very hopeful as a new antitumor drug.

The quinone derivatives which are isolated from extracts of Bignoniaceae *tabebuia* plant of the following formulae:

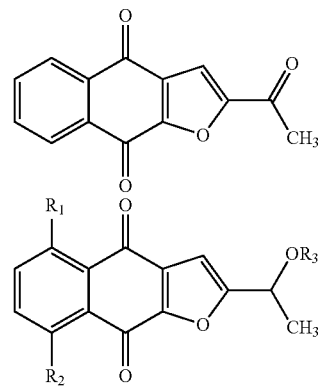

wherein $R_1$, $R_2$ and $R_3$ are H; $R_1$ and $R_3$ are H, $R_2$ is OH; $R_1$ is OH, $R_2$ and $R_3$ are H; $R_1$ and $R_2$ are H, $R_3$ is $COCH_3$; or $R_1$ and $R_2$ are H, $R_3$ is $COC(CF_3)OCH_3)CH_5$, have been already known to have an anti-tumor activity (Non-Patent Reference 5). However, a quinone derivative having more potent anti-tumor activity has been desired.

In the past, the following compounds described in Patent References 1 to 4 for example have been known as a naphtho[2,3-b]furan derivative. Patent Reference 1 discloses the following compound:

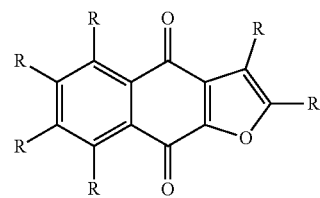

wherein R is —OR', —R', —CO—R', or —OCO—R', and R' is a hydrogen atom, an alkyl group and/or a hydroxyalkyl group.

Patent Reference 2 discloses the following compound:

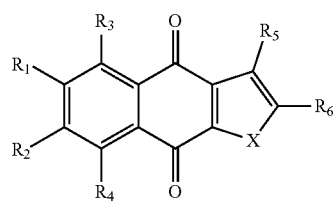

wherein X is —O—, —S—, or —$NR_8$—; $R_1$ and $R_2$ are independently H, a $C_1$-$C_4$ alkyl, and the like; $R_3$ is —$OR_9$; $R_4$ is H, a halogen or —$OR_9$; $R_5$ and $R_6$ are independently defined as $R_1$ and $R_2$; $R_8$ is H, a straight or branched chain $C_1$-$C_{18}$ alkyl, phenyl or benzyl which is un-substituted or substituted with a $C_1$-$C_4$ alkyl or a $C_1$-$C_4$ alkoxy; $R_9$ is hydrogen, a $C_1$-$C_{12}$ alkyl, or the like; $R_{10}$ is H, a $C_1$-$C_{18}$ alkyl, or the like; and $R_{11}$ is H, a $C_1$-$C_4$ alkyl or phenyl.

Patent Reference 3 discloses the following compound:

wherein R is a $C_1$-$C_6$ alkyl.

Patent Reference 4 discloses the following compound:

wherein X is O or S, $R^1$ is hydrogen, halogen, cyano, nitro, $CF_3$, $OCF_3$, alkyl or substituted alkyl, or the like, $R^3$ is hydrogen, cyano, $CF_3$, $OCF_3$, alkyl or substituted alkyl, and the like, $R^7$ is hydrogen, halogen, cyano, nitro, $CF_3$, $OCF_3$, alkyl or substituted alkyl, or the like, n is 1 to 4, provided that when $R_3$ is not $NR_bN_c$, then $R^7$ is not hydrogen and at least one of $R^1$ and $R^7$ is halogen, an aryl or substituted aryl. However, Patent References 1 to 4 never disclose the present compound of formula (1).

PRIOR ART

Patent Reference

Patent Reference 1: JP 63(1988)-196576 A
Patent Reference 2: JP 6(1994)-199787 A
Patent Reference 3: WO 2006/098355
Patent Reference 4: WO 2009/036059

Non-Patent Reference

Non-Patent Reference 1: Boman et al., *Journal of Clinical Oncology* 26(17): 2795-2799. 2008
Non-Patent Reference 2: Lobo et al. *Annu Rev Cell Dev Biol* 23: 675-99. 2007
Non-Patent Reference 3: Al-Hajj et al. *Oncogene* 23(43): 7274-82. 2004
Non-Patent Reference 4: Ponti et al. *Cancer Res* 65(13): 5506-11. 2005
Non-Patent Reference 5: Rao et al. *J Nat Prod* 45(5): 600-4. 1982

SUMMARY OF INVENTION

Technical Problem

A problem to be solved by the present invention is to provide a compound targeting a CSC which plays a large role in the continuing proliferation of malignant tumor, the metastasis of cancer, and the relapse and the resistance for an antitumor drug; and provide a compound inhibiting the growth of cancer cells which are non-CSCs and also suppressing the sphere-forming ability of cancer cells; and thereby providing a compound which is extremely useful as a novel antitumor-drug and has an excellent solubility.

Solution to Problem

The present inventors focused on the above-mentioned derivative, extensively studied on its antitumor activity, and then have found that the following compound of Formula (1) or a pharmaceutically acceptable salt thereof (hereinafter, optionally referred to as "the present compound") exhibits excellent effects in suppressing the proliferation and sphereforming ability of cancer cells, and is thus extremely useful as a novel antitumor-drug. On the basis of the new findings, the present invention has been completed.

In specific, the present invention is as follows:
Term 1:
A compound of Formula (1):

or a pharmaceutically acceptable salt thereof
wherein
X is an oxygen atom, a sulfur atom, or $NR^7$;
Y is —CO—, —CS—, —SO—, or —SO$_2$—;
$R^1$ is a hydrogen atom, a halogen atom, a cyano group, a nitro group, an optionally-substituted $C_{1-6}$ alkyl group, an optionally-substituted $C_{1-6}$ alkoxy group, an optionally-substituted amino group, an optionally-substituted $C_{1-6}$ alkylcarbonyl group, an optionally-substituted $C_{3-10}$ cycloalkyl group, an optionally-substituted $C_{3-10}$ cycloalkylcarbonyl group, an optionally-substituted 3- to 8-membered saturated heterocyclic group, an optionally-substituted 3- to 8-membered saturated heterocyclic carbonyl group, an optionally-substituted $C_{6-10}$ aryl group, an optionally-substituted $C_{6-10}$ arylcarbonyl group, an optionally-substituted 5- to 12-membered monocyclic or polycyclic heteroaryl group, or an optionally-substituted 5- to 12-membered monocyclic or polycyclic heteroarylcarbonyl group;

$R^2$ is a hydrogen atom, a hydroxy group, an optionally-substituted $C_{1-6}$ alkyl group, an optionally-substituted $C_1$ alkoxy group, an optionally-substituted amino group, an optionally-substituted $C_{3-10}$ cycloalkyl group, an optionally-substituted 3- to 8-membered saturated heterocyclic group, an optionally-substituted $C_{6-10}$ aryl group, or an optionally-substituted 5- to 12-membered monocyclic or polycyclic heteroaryl group; $R^3$, $R^4$, $R^5$, and $R^6$ are independently a hydrogen atom, a halogen atom, a cyano group, a nitro group, a hydroxy group, an optionally-substituted $C_{1-6}$ alkyl group, an optionally-substituted $C_{2-6}$ alkenyl group, an optionally-substituted $C_{2-6}$ alkynyl group, an optionally-substituted $C_{1-6}$ alkoxy group, an optionally-substituted $C_{1-6}$ alkylthio group, an optionally-substituted $C_{6-10}$ arylthio group, an optionally-substituted 5- to 12-membered monocyclic or polycyclic heteroarylthio group, an optionally-substituted $C_{1-6}$ alkylsulfinyl group, an optionally-substituted $C_{6-10}$ arylsulfinyl group, an optionally-substituted 5- to 12-membered monocyclic or polycyclic heteroarylsulfinyl group, an optionally-substituted $C_{1-6}$ alkylsulfonyl group, an optionally-substituted $C_{6-10}$ arylsulfonyl group, an optionally-substituted 5- to 12-membered monocyclic or polycyclic heteroarylsulfonyl group, an optionally-substituted amino group, an optionally-substituted $C_{1-6}$ alkylcarbonyl group, an optionally-substituted $C_{3-10}$ cycloalkyl group, an optionally-substituted $C_{3-10}$ cycloalkenyl group, an optionally-substituted 3- to 8-membered saturated heterocyclic group, an optionally-substituted $C_{6-10}$ aryl group, an optionally-substituted 5- to 12-membered monocyclic or polycyclic heteroaryl group, a $C_{1-6}$ alkylsulfinyl group, an optionally-substituted $C_{3-10}$ cycloalkylsulfinyl group, an optionally-substituted $C_{1-6}$ alkylsulfonyl group, or an optionally-substituted $C_{3-10}$ cycloalkylsulfonyl group; and $R^7$ is a hydrogen atom, an optionally-substituted $C_1$ s alkyl group, an optionally-substituted $C_{1-6}$ alkylcarbonyl group, an optionally-substituted $C_{3-10}$ cycloalkyl group, an optionally-substituted 3- to 8-membered saturated heterocyclic group, an optionally-substituted $C_{6-10}$ aryl group, or an optionally-substituted 5- to 12-membered monocyclic or polycyclic heteroaryl group;

provided that the following compounds are excluded: compounds wherein Y is —CO— and $R^1$ is a methyl group, 3-(furan-2-carbonyl)-2-(trifluoromethyl)naphtho[2,3-b]furan-4,9-dione,
3-(2-naphthoyl)-2-(trifluoromethyl)naphtho[2,3-b]furan-4,9-dione,
ethyl 4,9-dioxo-2-(trifluoromethyl)-4,9-dihydronaphtho[2,3-b]furan-3-carboxylate,
3-(2,3-dihydrobenzo[b][1,4]dioxine-6-carbonyl)-2-(trifluoromethyl)naphtho[2,3-b]furan-4,9-dione,
3-isonicotinoyl-2-(trifluoromethyl)naphtho[2,3-b]furan-4,9-dione,
3-(benzo[d][1,3]dioxole-5-carbonyl)-2-(trifluoromethyl)naphtho[2,3-b]furan-4,9-dione,
3-(4-methoxybenzoyl)-2-(trifluoromethyl)naphtho[2,3-b]furan-4,9-dione,
3-(3,4-dimethoxybenzoyl)-2-(trifluoromethyl)naphtho[2,3-b]furan-4,9-dione,
3-benzoyl-2-(trifluoromethyl)naphtho[2,3-b]furan-4,9-dione,
3-(4-bromobenzoyl)-2-(trifluoromethyl)naphtho[2,3-b]furan-4,9-dione,
2-(trifluoromethyl)-3-(3,4,5-trimethoxybenzoyl)naphtho[2,3-b]furan-4,9-dione,
3-(4-fluorobenzoyl)-2-(trifluoromethyl)naphtho[2,3-b]furan-4,9-dione, and
3-(thiophene-2-carbonyl)-2-(trifluoromethyl)naphtho[2,3-b]furan-4,9-dione.

Term 2:
The compound of Term 1 or a pharmaceutically acceptable salt thereof wherein X is an oxygen atom.

Term 3:
The compound of Term 1 or 2, or a pharmaceutically acceptable salt thereof wherein Y is —CO— or —SO$_2$—.

Term 4:
The compound of Term 3 or a pharmaceutically acceptable salt thereof wherein Y is —CO—.

Term 5:
The compound of Term 3 or a pharmaceutically acceptable salt thereof wherein Y is —SO$_2$—.

Term 6:
The compound of any one of Terms 1 to 5, or a pharmaceutically acceptable salt thereof wherein $R^1$ is an optionally-substituted $C_{1-6}$ alkyl group, an optionally-substituted $C_{1-6}$ alkylcarbonyl group, an optionally-substituted $C_{6-10}$ aryl group, or an optionally-substituted 5- to 12-membered monocyclic or polycyclic heteroaryl group.

Term 7:
The compound of Term 6 or a pharmaceutically acceptable salt thereof wherein $R^1$ is:
(1) a $C_{1-6}$ alkyl group optionally substituted with (a) 1 to 3 halogen atoms, (b) a hydroxy group, (c) 1 to 2 $C_{1-4}$ alkoxy groups, or (d) a 4- to 7-membered cyclic amino group,
(2) a $C_{1-6}$ alkylcarbonyl group optionally substituted with (a) 1 to 3 halogen atoms, (b) a hydroxy group, (c) 1 to 2 $C_{1-4}$ alkoxy groups, or (d) a 4- to 7-membered cyclic amino group,
(3) a $C_{6-10}$ aryl group optionally substituted with a halogen atom or 1 to 2 $C_{1-4}$ alkoxy groups, or
(4) a 5- to 12-membered monocyclic or polycyclic heteroaryl group optionally substituted with (a) 1 to 3 halogen atoms, (b) a hydroxy group, (c) a carboxy group, (d) a cyano group, (e) a $C_{1-4}$ alkylsulfonyl group, (f) a $C_{1-4}$ alkyl group optionally substituted with a carboxy group or a 4- to 7-membered cyclic amino group, (g) 1 to 3 $C_{1-4}$ alkoxy groups, (h) an amino group optionally substituted with 1 to 2 $C_{1-6}$ alkyl groups, or (i) a 4- to 7-membered cyclic amino group.

Term 8:
The compound of Term 7 or a pharmaceutically acceptable salt thereof wherein $R^1$ is:
(1) a $C_{1-6}$ alkyl group optionally substituted with (a) 1 to 3 halogen atoms, or (b) a hydroxy group.
(2) a $C_{1-6}$ alkylcarbonyl group, or
(3) a 5- to 12-membered monocyclic or polycyclic heteroaryl group optionally substituted with (a) 1 to 3 halogen atoms, (b) a cyano group, or (c) 1 to 3 $C_{1-4}$ alkoxy groups.

Term 9:
The compound of any one of Terms 1 to 8, or a pharmaceutically acceptable salt thereof wherein $R^2$ is an optionally-substituted $C_{1-6}$ alkyl group, an optionally-substituted $C_{1-6}$ alkoxy group, an optionally-substituted amino group, an optionally-substituted $C_{6-10}$ aryl group, or an optionally-substituted 3- to 8-membered saturated heterocyclic group.

Term 10:
The compound of Term 9 or a pharmaceutically acceptable salt thereof wherein $R^2$ is:
(1) an optionally-substituted $C_{1-6}$ alkyl group,
(2) a $C_{1-6}$ alkoxy group,
(3) an amino group optionally substituted with 1 to 2 $C_{1-6}$ alkyl groups,
(4) a 4- to 7-membered cyclic amino group optionally substituted with (a) 1 to 3 halogen atoms, (b) a hydroxy group, (c) a $C_{1-4}$ alkylsulfonyl group, (d) a $C_{1-4}$ alkyl group optionally substituted with a carboxy group or a 4- to 7-membered cyclic amino group, (e) 1 to 3 $C_{1-4}$ alkoxy groups, or (f) a 4- to 7-membered cyclic amino group,
(5) a $C_{6-10}$ aryl group optionally substituted with (a) 1 to 3 halogen atoms, (b) a hydroxy group, (c) a carboxy group, (d) a cyano group, (e) a $C_{1-4}$ alkylsulfonyl group, (f) a $C_{1-4}$ alkyl group optionally substituted with a carboxy group or a 4- to 7-membered cyclic amino group, (g) 1 to 3 $C_{1-4}$ alkoxy groups, or (h) a 4- to 7-membered cyclic amino group, or
(6) a 3- to 8-membered saturated heterocyclic group optionally substituted with (a) 1 to 3 halogen atoms, (b) a hydroxy group, (c) a carboxy group, (d) a $C_{1-4}$ alkylsulfonyl group, (e) a $C_{1-4}$ alkyl group optionally substituted with a carboxy group or a 4- to 7-membered cyclic amino group. (f) 1 to 3 $C_{1-4}$ alkoxy groups, or (g) a 4- to 7-membered cyclic amino group.

Term 11:

The compound of Term 10 or a pharmaceutically acceptable salt thereof wherein $R^2$ is:

(1) a $C_{1-6}$ alkyl group optionally substituted with an optionally-substituted 4- to 7-membered cyclic amino group, or a mono- or di-substituted amino group, (2) an amino group optionally substituted with a $C_{1-6}$ alkyl group, or (3) a 4- to 7-membered cyclic amino group optionally substituted with 1 to 2 $C_{1-6}$ alkyl groups.

Term 12:

The compound of any one of Terms 1 to 11, or a pharmaceutically acceptable salt thereof wherein $R^3$, $R^4$, $R^5$, and $R^6$ are independently a hydrogen atom, a halogen atom, a hydroxy group, or a $C_{1-6}$ alkoxy group.

Term 13:

The compound of Term 12 or a pharmaceutically acceptable salt thereof wherein $R^3$, $R^4$, $R^5$, and $R^6$ are a hydrogen atom.

Term 14:

The compound of Term 1 or a pharmaceutically acceptable salt thereof wherein the compound is selected from the following group:

methyl 2-(1,1-dimethoxyethyl)-4,9-dioxo-4,9-dihydronaphtho[2,3-b]furan-3-carboxylate,
methyl 2-acetyl-4,9-dioxo-4,9-dihydronaphtho[2,3-b]furan-3-carboxylate.
2-acetyl-4,9-dioxo-4,9-dihydronaphtho[2,3-b]furan-3-carboxylic acid,
2-acetyl-N,N-dimethyl-4,9-dioxo-4,9-dihydronaphtho[2,3-b]furan-3-carboxamide,
2-acetyl-3-(4-methylpiperazine-1-carbonyl)naphtho[2,3-b]furan-4,9-dione hydrochloride,
methyl 4,9-dioxo-2-(trifluoromethyl)-4,9-dihydronaphtho[2,3-b]furan-3-carboxylate,
4,9-dioxo-2-(trifluoromethyl)-4,9-dihydronaphtho[2,3-b]furan-3-carboxylic acid,
3-(4-methylpiperazine-1-carbonyl)-2-(trifluoromethyl)naphtho[2,3-b]furan-4,9-dione,
methyl 2-(4-fluorophenyl)-4,9-dioxo-4,9-dihydronaphtho[2,3-b]furan-3-carboxylate,
2-(4-fluorophenyl)-4,9-dioxo-4,9-dihydronaphtho[2,3-b]furan-3-carboxylic acid,
2-(4-fluorophenyl)-N,N-dimethyl-4,9-dioxo-4,9-dihydronaphtho[2,3-b]furan-3-carboxamide,
methyl 4,9-dioxo-2-(pyridin-3-yl)-4,9-dihydronaphtho[2,3-b]furan-3-carboxylate,
2-(1,1-dimethoxyethyl)-3-(morpholine-4-carbonyl)naphtho[2,3-b]furan-4,9-dione,
2-acetyl-3-(morpholine-4-carbonyl)naphtho[2,3-b]furan-4,9-dione,
methyl 2-(chloromethyl)-4,9-dioxo-4,9-dihydronaphtho[2,3-b]furan-3-carboxylate,
methyl 2-(morpholinomethyl)-4,9-dioxo-4,9-dihydronaphtho[2,3-b]furan-3-carboxylate,
2-(1,1-dimethoxyethyl)-3-((4-methylpiperazine-1-yl)sulfonyl)naphtho[2,3-b]furan-4,9-dione.
2-acetyl-3-((4-methylpiperazine-1-yl)sulfonyl)naphtho[2,3-b]furan-4,9-dione,
2-(1,1-dimethoxyethyl)-3-(phenylsulfonyl)naphtho[2,3-b]furan-4,9-dione,
2-acetyl-3-(phenylsulfonyl)naphtho[2,3-b]furan-4,9-dione, and
N,N-dimethyl-4,9-dioxo-2-(trifluoromethyl)-4,9-dihydronaphtho[2,3-b]furan-3-carboxamide.

Term 15:

A pharmaceutical composition comprising the compound of any one of Terms 1 to 14, or a pharmaceutically acceptable salt thereof.

Term 16:

An anticancer agent comprising the compound of any one of Terms 1 to 14, or a pharmaceutically acceptable salt thereof.

Term 17:

The anticancer agent of Term 16 for treating hematological cancer, myeloma, liver cancer, ovarian cancer, prostate cancer, lung cancer, osteosarcoma, colon cancer, breast cancer, skin cancer, or epithelial cell cancer.

Term 18:

A method for preventing or treating cancer which comprises administering an effective amount of the compound of any one of Terms 1 to 14, or a pharmaceutically acceptable salt thereof.

Term 19:

The method of Term 18 wherein the cancer is hematological cancer, myeloma, liver cancer, ovarian cancer, prostate cancer, lung cancer, osteosarcoma, colon cancer, breast cancer, skin cancer, or epithelial cell cancer.

Term 20:

The compound of any one of Terms 1 to 14, or a pharmaceutically acceptable salt thereof for use in preventing or treating cancer.

Term 21:

The compound of Term 20 or a pharmaceutically acceptable salt thereof wherein the cancer is hematological cancer, myeloma, liver cancer, ovarian cancer, prostate cancer, lung cancer, osteosarcoma, colon cancer, breast cancer, skin cancer, or epithelial cell cancer.

Effects of Invention

The present compound exhibits excellent effects in suppressing the proliferation and sphere-forming ability of cancer cells, and can be preferably used as an antitumor drug or cell growth inhibitor. Furthermore, the present compound has an excellent solubility and thus can be administered orally or parenterally (e.g. intravenously, subcutaneously, by intramuscular injection, locally, transrectally, percutaneously, and nasally), thereby used for preventing or treating diseases or conditions which may be related to proliferation of cells (e.g. cancer).

DESCRIPTION OF EMBODIMENTS

Hereinafter, the present invention is explained in more detail. The number of substituents of a group defined by the term "optionally substituted" as used herein is 1 or more, and not limited as long as the substitution is possible. Unless otherwise indicated, the explanation of each group is applied to cases where the group is a part of another group or a substituent. The number of carbon atoms in the definition of the substituents may be optionally shown as "$C_{1-6}$". For example, the term "$C_{1-6}$ alkyl" means an alkyl group with 1 to 6 carbon atoms. Unless otherwise indicated, a substituent defined by neither "optionally substituted" nor "substituted" means that the substituent is "unsubstituted".

The term "halogen atom" as used herein includes, for example, fluorine, chlorine, bromine and iodine atoms; and preferably fluorine and chlorine atoms.

The term "$C_{1-6}$ alkyl group" as used herein refers to a straight or branched saturated hydrocarbon group with 1 to 6 carbon atoms, and includes preferably a $C_{1-4}$ alkyl group and the like. In specific, the "$C_{1-6}$ alkyl group" includes methyl, ethyl, propyl, 1-methylethyl, butyl, 2-methylpropyl, 1-methylpropyl, 1,1-dimethylethyl, pentyl, 3-methylbutyl, 2-methylbutyl, 2,2-dimethylpropyl, 1-ethylpropyl, 1,1-dimethylpropyl, hexyl, 4-methylpentyl, 3-methylpentyl, 2-methylpentyl, 1-methylpentyl and the like.

The term "$C_{2-6}$ alkenyl group" as used herein refers to a straight or branched unsaturated hydrocarbon group with 2 to 6 carbon atoms containing one double bond; and specifically includes vinyl, propenyl, methylpropenyl, butenyl, methylbutenyl and the like.

The term "$C_{2-6}$ alkynyl group" as used herein refers to a straight or branched unsaturated hydrocarbon group with 2 to 6 carbon atoms containing one triple bond; and specifically includes ethinyl, 1-propynyl, 2-propynyl, 2-butynyl, pentynyl, hexynyl and the like.

The term "$C_{3-10}$ cycloalkyl group" as used herein refers to a cyclic saturated hydrocarbon group with 3 to 10 carbon atoms, and includes preferably a $C_{3-7}$ cycloalkyl group and the like. In specific, the "$C_{3-10}$ cycloalkyl group" includes cyclopropyl, cyclobutyl, cyclopentyl, cyclohexyl, cycloheptyl and the like. The "$C_{3-10}$ cycloalkyl group" also includes those wherein the cycloalkyl group is taken together with an aromatic ring to form a condensed ring having 10 carbon atoms or less in the ring, such as those shown below:

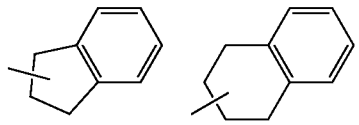

The term "$C_{3-10}$ cycloalkenyl group" as used herein refers to a cyclic unsaturated hydrocarbon group with 3 to 10 carbon atoms containing one double bond, and preferably includes a $C_{3-7}$ cycloalkenyl group. In specific, the "$C_{3-10}$ cycloalkenyl group" includes cyclopropenyl, cyclobutenyl, cyclopentenyl, cyclohexenyl, cycloheptenyl group and the like.

The term "$C_{1-6}$ alkoxy group" as used herein has a $C_{1-6}$ alkyl moiety as defined in the above-shown "$C_{1-6}$ alkyl group", and includes preferably a $C_{1-4}$ alkoxy group and the like. In specific, the "$C_{1-6}$ alkoxy group" includes methoxy, ethoxy, propoxy, 1-methylethoxy, butoxy, 2-methylpropoxy, 1-methylpropoxy, 1,1-dimethylethoxy, pentyloxy, 3-methylbutoxy, 2-methylbutoxy, 2,2-dimethylpropoxy, 1-ethylpropoxy, 1,1-dimethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy and the like.

The term "$C_{1-6}$ alkylthio group" as used herein has a $C_{1-4}$ alkyl moiety as defined in the above-shown "$C_{1-6}$ alkyl group", and includes preferably a $C_{1-4}$ alkylthio group and the like. In specific, the "$C_{1-6}$ alkylthio group" includes methylthio, ethylthio, propylthio, isopropylthio, butylthio, sec-butylthio, tert-butylthio, pentylthio, hexylthio and the like.

The term "$C_{1-6}$ alkylsulfinyl group" as used herein has a $C_{1-6}$ alkyl moiety as defined in the above-shown "$C_{1-6}$ alkyl group", and includes preferably a $C_{1-4}$ alkylsulfinyl group and the like. In specific, the "$C_{1-6}$ alkylsulfinyl group" includes methylsulfinyl, ethylsulfinyl, propylsulfinyl, isopropylsulfinyl, butylsulfinyl, pentylsulfinyl, hexylsulfinyl and the like.

The term "$C_{1-6}$ alkylsulfonyl group" as used herein has a $C_{1-6}$ alkyl moiety as defined in the above-shown "$C_{1-6}$ alkyl group", and includes preferably a $C_{1-4}$ alkylsulfonyl group and the like. In specific, the "$C_{1-6}$ alkylsulfonyl group" includes methylsulfonyl, ethylsulfonyl, propylsulfonyl, isopropylsulfonyl, butylsulfonyl, pentylsulfonyl, hexylsulfonyl and the like.

The term "$C_{1-6}$ alkylcarbonyl group" as used herein has a $C_{1-6}$ alkyl moiety as defined in the above-shown "$C_{1-6}$ alkyl group", and includes preferably a $C_{1-4}$ alkylcarbonyl group and the like. In specific, the "$C_{1-6}$ alkylcarbonyl group" includes methylcarbonyl, ethylcarbonyl, propylcarbonyl, 1-methylethylcarbonyl, butylcarbonyl, 2-methylpropylcarbonyl, 1-methylpropylcarbonyl, 1,1-dimethylethylcarbonyl and the like.

The term "$C_{3-10}$ cycloalkoxy group" as used herein has a $C_{3-10}$ cycloalkyl moiety as defined in the above-shown "$C_{3-10}$ cycloalkyl group", and includes preferably a $C_{3-7}$ cycloalkoxy group and the like. In specific, the "$C_{3-10}$ cycloalkoxy group" includes cyclopropoxy, cyclobutoxy, cyclopentyloxy, cyclohexyloxy, cycloheptyloxy and the like.

The term "$C_{3-10}$ cycloalkylsulfinyl group" as used herein has a $C_{3-10}$ cycloalkyl moiety as defined in the above-shown "$C_{3-10}$ cycloalkyl group", and includes preferably a $C_{3-7}$ cycloalkylsulfinyl group and the like. In specific, the "$C_{3-10}$ cycloalkylsulfinyl group" includes cyclopropylsulfinyl, cyclobutylsulfinyl, cyclopentylsulfinyl, cyclohexylsulfinyl, cycloheptylsulfinyl and the like.

The term "$C_{3-10}$ cycloalkylsulfonyl group" as used herein has a $C_{3-10}$ cycloalkyl moiety as defined in the above-shown "$C_{3-10}$ cycloalkyl group", and includes preferably a $C_{3-7}$ cycloalkylsulfonyl group. In specific, the "$C_{3-10}$ cycloalkylsulfonyl group" includes cyclopropylsulfonyl, cyclobutylsulfonyl, cyclopentylsulfonyl, cyclohexylsulfonyl, cycloheptylsulfonyl and the like.

The term "$C_{3-10}$ cycloalkylcarbonyl group" as used herein refers to a carbonyl group substituted with the above-shown "$C_{3-10}$ cycloalkyl group"; and specifically includes cyclopropylcarbonyl, cyclobutylcarbonyl, cyclopentylcarbonyl, cyclohexylcarbonyl, cycloheptylcarbonyl and the like.

The term "$C_{3-10}$ cycloalkoxycarbonyl group" as used herein refers to a carbonyl group substituted with the above-shown "$C_{3-10}$ cycloalkoxy group"; and specifically includes cyclopropyloxycarbonyl, cyclobutyloxycarbonyl, cyclopentyloxycarbonyl, cyclohexyloxycarbonyl, cycloheptyloxycarbonyl and the like.

The term "$C_{1-6}$ alkylcarbonyloxy group" as used herein has a $C_{1-6}$ alkylcarbonyl moiety as defined in the above-shown "$C_{1-6}$ alkylcarbonyl group", and includes preferably a $C_{1-4}$ alkylcarbonyloxy group and the like. In specific, the "$C_{1-6}$ alkylcarbonyloxy group" includes methylcarbonyloxy, ethylcarbonyloxy, propylcarbonyloxy, 1-methylethyl-carbonyloxy, butylcarbonyloxy, 2-methylpropylcarbonyloxy, 1-methylpropylcarbonyloxy, 1,1-dimethylethylcarbonyloxy and the like.

The term "$C_{1-6}$ alkoxycarbonyl group" as used herein has a $C_{1-6}$ alkoxy moiety as defined in the above-shown "$C_{1-6}$ alkoxy group"; and specifically includes methoxycarbonyl, ethoxycarbonyl and the like.

The term "$C_{6-10}$ aryl group" as used herein refers to an aromatic hydrocarbon with 6 to 10 carbon atoms; and specifically includes phenyl, 1-naphthyl, 2-naphthyl and the like. An aryl group includes typically a $C_{6-10}$ aryl group, and preferably a $C_6$ or $C_{10}$ aryl group. The "$C_{6-10}$ aryl group" also includes those wherein the aromatic ring is taken together with a Ca cycloalkyl group or with, for example, a 5- to 6-membered heterocyclic group comprising 1 to 3 atoms independently selected from nitrogen, oxygen and sulfur atoms to form a condensed ring having 10 carbon atoms or less in the ring, such as those shown below:

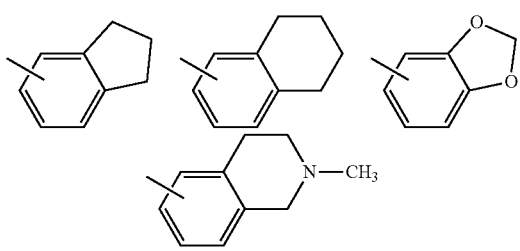

The term "$C_{7-14}$ aralkyl group" as used herein refers to a $C_{6-10}$ aryl$C_{1-4}$ alkyl group (i.e. a $C_{1-4}$ alkyl group as defined above which is substituted with the above-shown "$C_{6-10}$ aryl group"), and preferably includes a $C_{7-10}$ aralkyl group (i.e. a phenyl$C_{1-4}$ alkyl group). In specific, the "$C_{7-14}$ aralkyl group" includes benzyl, 2-phenylethyl, 1-phenylpropyl, 1-naphthylmethyl and the like.

The term "heteroaryl group" as used herein includes, for example, a 5- to 12-membered monocyclic or polycyclic group comprising one or more (e.g. 1 to 4) heteroatoms independently selected from nitrogen, sulfur and oxygen atoms. The "heteroaryl group" includes preferably a 5- to 10-membered monocyclic or polycyclic group and the like, and more preferably a 5- or 6-membered monocyclic heteroaryl group and the like. In specific, the "heteroaryl group" includes pyrrolyl, thienyl, benzothienyl, benzofuranyl, benzoxazolyl, benzothiazolyl, furyl, oxazolyl, thiazolyl, isoxazolyl, isothiazolyl, benzisoxazolyl, benzisothiazolyl, imidazolyl, pyrazolyl, pyridyl, pyrazyl, pyrimidyl, pyridazyl, quinolyl, isoquinolyl, triazolyl, triazinyl, tetrazolyl, indolyl, imidazo[1,2-a]pyridyl, pyrazolo[1,5-a]pyridyl, [1,2,4]triazolo[1,5-a]pyridyl, benzimidazolyl, quinoxalyl, cinnolyl, quinazolyl, indazolyl, naphthyridyl, quinolinolyl, isoquinolinolyl and the like.

The term "$C_{6-10}$ arylthio group" as used herein has a $C_{6-10}$ aryl moiety as defined in the above-shown "$C_{6-10}$ aryl group"; and specifically includes phenylthio, 1-naphthylthio, 2-naphthylthio and the like.

The term "$C_{6-10}$ arylsulfinyl group" as used herein has a $C_{6-10}$ aryl moiety as defined in the above-shown "$C_{6-10}$ aryl group"; and specifically includes phenylsulfinyl, 1-naphthylsulfinyl, 2-naphthylsulfinyl and the like.

The term "$C_{6-10}$ arylsulfonyl group" as used herein has a $C_{6-10}$ aryl moiety as defined in the above-shown "$C_{6-10}$ aryl group", and includes phenylsulfonyl and the like.

The term "$C_{6-10}$ arylcarbonyl group" as used herein refers to a carbonyl group substituted with the above-shown "$C_{6-10}$ aryl group"; and includes preferably a $C_6$ aryl-carbonyl group (i.e. a phenylcarbonyl group). In specific, the "$C_{6-10}$ arylcarbonyl group" includes benzoyl, 1-naphthoyl, 2-naphthoyl and the like.

The term "5- to 12-membered monocyclic or polycyclic heteroarylthio group" as used herein has a 5- to 12-membered monocyclic or polycyclic heteroaryl moiety as defined in the above-shown "5- to 12-membered monocyclic or polycyclic heteroaryl group"; and specifically includes pyrrolylthio, thienylthio, benzothienylthio, benzofuranylthio, benzoxazolylthio, benzothiazolylthio, furylthio, oxazolylthio, thiazolylthio, isoxazolylthio, isothiazolylthio, benzisoxazolylthio, benzisothiazolylthio, imidazolylthio, pyrazolylthio, pyridylthio and the like.

The term "5- to 12-membered monocyclic or polycyclic heteroarylsulfinyl group" as used herein has a 5- to 12-membered monocyclic or polycyclic heteroaryl moiety as defined in the above-shown "5- to 12-membered monocyclic or polycyclic heteroaryl group"; and specifically includes pyrrolylsulfinyl, thienylsulfinyl, benzothienylsulfinyl, benzofuranylsulfinyl, benzoxazolylsulfinyl, benzothiazolylsulfinyl, furylsulfinyl, oxazolylsulfinyl, thiazolylsulfinyl, isoxazolylsulfinyl, isothiazolylsulfinyl, benzisoxazolylsulfinyl, benzisothiazolylsulfinyl, imidazolylsulfinyl, pyrazolylsulfinyl, pyridylsulfinyl and the like.

The term "5- to 12-membered monocyclic or polycyclic heteroarylsulfonyl group" as used herein has a 5- to 12-membered monocyclic or polycyclic heteroaryl moiety as defined in the above-shown "5- to 12-membered monocyclic or polycyclic heteroaryl group"; and specifically includes pyrrolylsulfonyl, thienylsulfonyl, benzothienylsulfonyl, benzofuranylsulfonyl, benzoxazolylsulfonyl, benzothiazolylsulfonyl, furylsulfonyl, oxazolylsulfonyl, thiazolylsulfonyl, isoxazolylsulfonyl, isothiazolylsulfonyl, benzisoxazolylsulfonyl, benzisothiazolylsulfonyl, imidazolylsulfonyl, pyrazolylsulfonyl, pyridylsulfonyl and the like.

The term "5- to 12-membered monocyclic or polycyclic heteroarylcarbonyl group" as used herein has a 5- to 12-membered monocyclic or polycyclic heteroaryl moiety as defined in the above-shown "5- to 12-membered monocyclic or polycyclic heteroaryl group"; and specifically includes pyrrolylcarbonyl, thienylcarbonyl, benzothienylcarbonyl, benzofuranylcarbonyl, benzoxazolylcarbonyl, benzothiazolylcarbonyl, furylcarbonyl, oxazolylcarbonyl, thiazolylcarbonyl, isoxazolylcarbonyl, isothiazolylcarbonyl, benzisoxazolylcarbonyl, benzisothiazolylcarbonyl, imidazolylcarbonyl, pyrazolylcarbonyl, pyridylcarbonyl and the like.

The term "3- to 8-membered saturated heterocyclic group" as used herein includes, for example, a 3- to 8-membered saturated heterocyclic group comprising 1 to 3 ring atoms independently selected from nitrogen, oxygen and sulfur atoms; preferably a 4- to 7-membered saturated heterocyclic group; and more preferably a 5- or 6-membered saturated heterocyclic group. The "heterocyclic group" includes pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, tetrahydropyridinyl, oxetanyl, tetrahydropyranyl and the like; and also includes those wherein the ring has a bridged structure. The "heterocyclic group" may comprise nitrogen as a ring atom, but the nitrogen is not used to bind other groups with the heterocyclic group, i.e. the "heterocyclic group" does not include a pyrrolidino group or the like.

The above-shown "saturated heterocyclic group" may be taken together with a 6-membered aromatic hydrocarbon or a 6-membered heteroaryl to form a condensed ring; and includes, for example, a bicyclic heterocyclic group wherein the above-shown "5- or 6-membered saturated heterocyclic group" is condensed with a 6-membered aromatic hydrocarbon or a 6-membered heteroaryl. The "6-membered aromatic hydrocarbon" herein includes benzene and the like. The "6-membered heteroaryl" herein includes pyridine, pyrimidine, pyridazine and the like. The "condensed ring" herein specifically includes dihydroindolyl, dihydroisoindolyl, dihydropurinyl, dihydrothiazolopyrimidinyl, dihydrobenzodioxanyl, isoindolyl, indazolyl, pyrrolidinyl, tetrahydroquinolinyl, decahydroquinolinyl, tetrahydrisoquinolinyl, decahydroisoquinolinyl, tetrahydronaphthyridinyl, tetrahydropyridoazepinyl and the like.

The term "3- to 8-membered saturated heterocyclic oxy group" as used herein has a saturated heterocyclic moiety as defined in the above-shown "saturated heterocyclic group"; and is preferably a 4- to 7-membered saturated heterocyclic oxy group, and more preferably a 5- or 6-membered saturated heterocyclic oxy group. In specific, the "3- to 8-membered saturated heterocyclic oxy group" includes 4-pyranyloxy and the like.

The term "$C_{3-10}$ cycloalkyl $C_{1-4}$ alkyl group" as used herein refers to a $C_{1-4}$ alkyl group substituted with the above-shown "$C_{3-10}$ cycloalkyl"; and specifically includes cyclopropylmethyl, cyclobutylmethyl, cyclopentylmethyl, cyclohexylmethyl and the like.

The term "3- to 8-membered saturated heterocyclic $C_{1-4}$ alkyl group" as used herein has a 3- to 8-membered saturated heterocyclic moiety as defined in the above-shown "3- to 8-membered saturated heterocyclic group", and specifically includes 4-pyranylmethyl and the like.

The term "3- to 8-membered saturated heterocyclic carbonyl group" as used herein has a 3- to 8-membered saturated heterocyclic moiety as defined in the above-shown "3- to 8-membered saturated heterocyclic group", and specifically includes 4-pyranylcarbonyl and the like.

The term "3- to 8-membered saturated heterocyclic oxycarbonyl group" as used herein has a 3- to 8-membered saturated heterocyclic moiety as defined in the above-shown "3- to 8-membered saturated heterocyclic group", and specifically includes 4-pyranyloxycarbonyl and the like.

The term "$C_{6-10}$ aryloxy group" as used herein has a $C_{6-10}$ aryl moiety as defined in the above-shown "$C_{6-10}$ aryl group", and includes preferably a $C_6$ aryloxy group (i.e. a phenoxy group). In specific, the "$C_{6-10}$ aryloxy group" includes phenoxy, 1-naphthoxy, 2-naphthoxy and the like.

The term "$C_{6-10}$ arylcarbonyloxy group" as used herein has a $C_{6-10}$ aryl moiety as defined in the above-shown "$C_{6-10}$ aryl group", and includes preferably a $C_6$ arylcarbonyloxy group (i.e. a phenylcarbonyloxy group). In specific, the "$C_{6-10}$ arylcarbonyloxy group" includes benzoyloxy, 1-naphthoyloxy, 2-naphthoyloxy and the like.

The term "$C_{6-10}$ aryloxycarbonyl group" as used herein refers to a carbonyl group substituted with the above-shown "$C_{6-10}$ aryloxy group", and includes preferably a $C_6$ aryloxycarbonyl group (i.e. a phenyloxycarbonyl group). In specific, the "$C_{6-10}$ aryloxycarbonyl group" includes phenoxycarbonyl, 1-naphthoxycarbonyl, 2-naphthoxycarbonyl and the like.

The term "5- or 6-membered monocyclic heteroaryl$C_{1-4}$ alkyl group" as used herein refers to a $C_{1-4}$ alkyl group substituted with the above-shown "5- or 6-membered monocyclic heteroaryl group", and specifically includes pyrrolylmethyl and the like.

The term "5- or 6-membered monocyclic heteroaryloxy group" as used herein has a 5- or 6-membered monocyclic heteroaryl moiety as defined in the above-shown "5- or 6-membered monocyclic heteroaryl", and specifically includes pyrrolylcarbonyl and the like.

The term "optionally-substituted amino group" as used herein includes an amino group, a mono- or di-substituted amino group, an optionally-substituted 4- to 7-membered cyclic amino group, and the like.

The term "mono- or di-substituted amino" as used herein means that the amino is substituted with substituent(s) such as the above-shown "$C_{1-6}$ alkyl", "$C_{3-10}$ cycloalkyl", "$C_{3-10}$ cycloalkyl $C_{1-4}$ alkyl", "3- to 8-membered saturated heterocyclic group", "3- to 8-membered saturated heterocyclic $C_{1-4}$ alkyl", "$C_{6-10}$ aryl", "$C_{7-14}$ aralkyl", "5- or 6-membered monocyclic heteroaryl". "5- or 6-membered monocyclic heteroaryl$C_{1-4}$ alkyl", and the like.

In specific, the term "mono-substituted amino" as used herein includes mono-$C_{1-6}$ alkylamino (e.g. methylamino, ethylamino, propylamino, 1-methylethylamino, butylamino, 2-methylpropylamino, 1-methylpropylamino, and 1,1-dimethylethylamino), $C_{3-10}$ cycloalkylamino (e.g. cyclopropylamino, cyclobutylamino, cyclopentylamino, cyclohexylamino, and cycloheptylamino), ($C_{3-10}$ cycloalkyl $C_{1-4}$ alkyl)amino (e.g. cyclopropylmethylamino, cyclobutylmethylamino, cyclopentylmethylamino, cyclohexylmethylamino, and cycloheptylmethylamino), $C_{6-10}$ arylamino (e.g. phenylamino, 1-naphthylamino, and 2-naphthylamino), $C_{7-14}$ aralkylamino (e.g. benzylamino, 1-naphthylmethylamino, and 2-naphthylmethylamino), 3- to 8-membered saturated heterocyclic amino (e.g. tetrahydropyranylamino, tetrahydropyridinylamino, pyrrolidinylamino, oxopyrrolidinylamino, tetrahydrofuranylamino, and piperidinylamino), (3- to 8-membered saturated heterocyclic $C_{1-4}$ alkyl)amino (e.g. tetrahydropyranylmethylamino, tetrahydropyridinylmethylamino, pyrrolidinylmethylamino, oxopyrrolidinylmethylamino, tetrahydrofuranylmethylamino, piperidinylmethylamino, piperazinylmethylamino, and morpholinylmethylamino), (5- or 6-membered monocyclic heteroaryl)amino (e.g. pyrrolylamino, thienylamino, furylamino, oxazolylamino, thiazolylamino, isoxazolylamino, isothiazolylamino, imidazolylamino, pyrazolylamino, triazolylamino, oxadiazolylamino, thiadiazolylamino, tetrazolylamino, pyridylamino, pyrazylamino, pyrimidylamino, pyridazylamino, and triazylamino), (5- or 6-membered monocyclic heteroaryl$C_{1-4}$ alkyl)amino (e.g. pyrrolylmethylamino, thienylmethylamino, furylmethylamino, oxazolylmethylamino, thiazolylmethylamino, isoxazolylmethylamino, isothiazolylmethylamino, imidazolylmethylamino, pyrazolylmethylamino, triazolylmethylamino, oxadiazolylmethylamino, thiadiazolylmethylamino, tetrazolylmethylamino, pyridylmethylamino, pyrazylmethylamino, pyrimidylmethylamino, pyridazylmethylamino, and triazylmethylamino) and the like.

In specific, the term "di-substituted amino" as used herein includes di-$C_{1-6}$ alkylamino (e.g. dimethylamino, diethylamino, dipropylamino, di-1-methylethylamino, dibutylamino, di-2-methylpropylamino, di-1-methylpropylamino, and di-1,1-dimethylethylamino), N—($C_{1-6}$ alkyl)-N—($C_{3-10}$ cycloalkyl)amino (e.g. methylcyclopropylamino, methylcyclobutylamino, methylcyclopentylamino, methylcyclohexylamino, and methylcycloheptylamino), N—($C_{1-6}$ alkyl)-N-(3- to 8-membered saturated heterocyclic)amino (e.g. methyltetrahydropyranylamino, methyltetrahydropyridinylamino, methylpyrrolidinylamino, methyloxopyrrolidinylamino, methyltetrahydrofuranylamino, and methylpiperidinylamino) and the like.

The term "4- to 7-membered cyclic amino group" as used herein includes, for example, a 4- to 7-membered cyclic amino group comprising 1 to 3 heteroatoms independently selected from nitrogen, oxygen and sulfur atoms; and includes preferably a 5- to 6-membered cyclic amino group. Note that the nitrogen in the "4- to 7-membered cyclic amino group" is used to attach the group to the parent molecular moiety. In specific, the "4- to 7-membered cyclic amino group" includes azetidino, pyrrolidino, imidazolidino, oxazolidino, thiazolidino, piperazino, piperidino, morpholino, thiomorpholino, azepano, oxoazepano and the like; and also includes cyclic amino groups with a partially unsaturated bond(s) in the ring, wherein the ring may form a bridged structure. The "cyclic amino groups with a partially unsaturated bond(s)" include dihydropyrrolino, tetrahydropyridino and the like. The "cyclic amino groups wherein the ring forms a bridged structure" include azabicyclooctano, azabicyclononano, oxoazabicyclononano, diazabicyclononano and the like.

The "4- to 7-membered cyclic amino group" or "5- to 6-membered cyclic amino group" may be taken together with a $C_{3-6}$ cycloalkyl group, a 6-membered aromatic hydrocarbon group, a 5- or 6-membered heterocyclic group or a 4- to 7-membered cyclic amino group to form a condensed ring; and such condensed ring specifically includes the groups shown below:

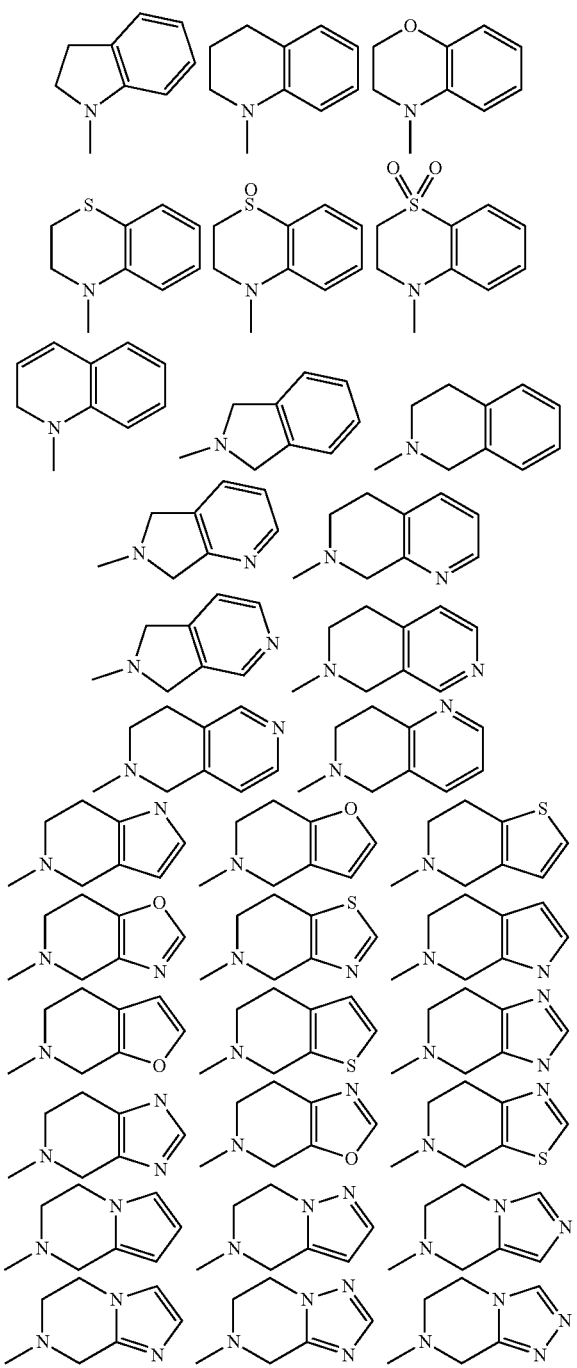

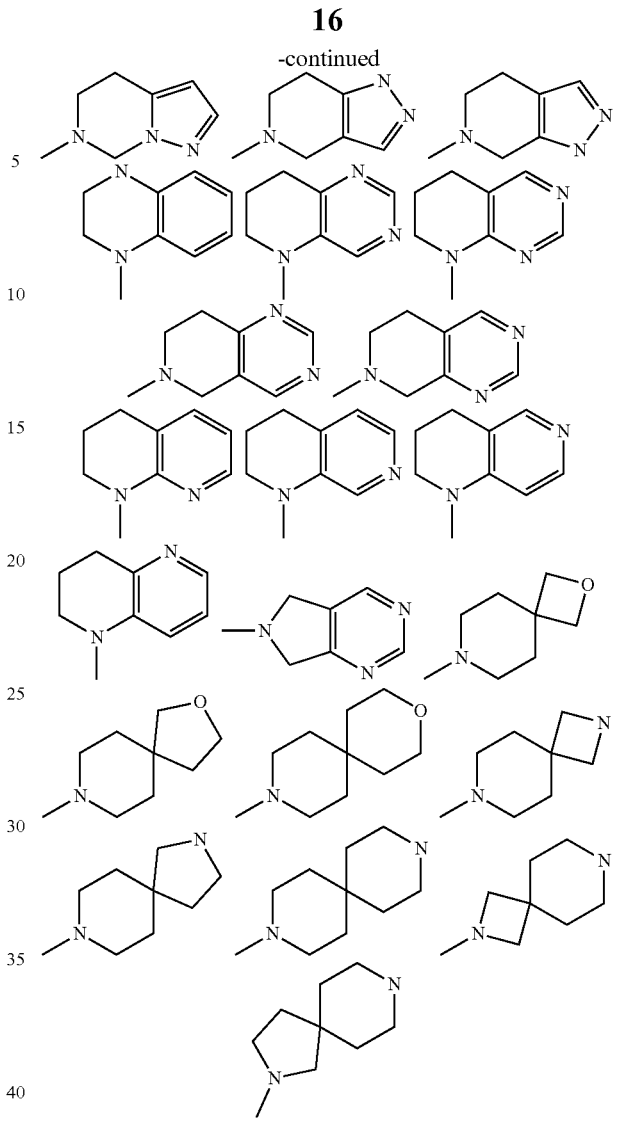

The term "aminocarbonyl group" as used herein refers to a carbonyl group substituted with the above-shown "amino group", i.e. the term "amino group" herein includes a mono-substituted amino group, di-substituted amino group and a 5- to 7-membered cyclic amino group.

The term "an optionally-substituted $C_{1-6}$ alkyl group" as used herein means that the $C_{1-6}$ alkyl group may be optionally substituted with, for example, the following substituents (a) to (ah):
(a) a halogen atom,
(b) a cyano group,
(c) a hydroxy group,
(d) a nitro group,
(e) a thiol group,
(f) a $C_{1-4}$ alkylthio group,
(g) a $C_{6-10}$ arylthio group,
(h) a $C_{1-6}$ alkylcarbonyl group,
(i) a $C_{1-6}$ alkylcarbonyloxy group,
(j) a $C_{6-10}$ arylcarbonyloxy group,
(k) a $C_{3-10}$ cycloalkyl group,
(l) a $C_{3-10}$ cycloalkoxy group,
(m) a $C_{3-10}$ cycloalkylcarbonyl group,
(n) a $C_{6-10}$ aryl group,
(o) a $C_{6-10}$ arylcarbonyl group, (p) a $C_{6-10}$ aryloxycarbonyl group,
(q) a carboxy group,
(r) an amino group optionally substituted with 1 to 2 groups independently selected from the group consisting of:
 (r1) a $C_{1-4}$ alkyl group,
 (r2) a $C_{3-10}$ cycloalkyl group,
 (r3) a $C_{6-10}$ cycloalkyl $C_{1-4}$ alkyl group,
 (r4) a 3- to 8-membered saturated heterocyclic group,
 (r5) a 3- to 8-membered saturated heterocyclic-$C_{1-4}$ alkyl group,
 (r6) a $C_{6-10}$ aryl group,
 (r7) a $C_{7-14}$ aralkyl group,
 (r8) a 5- or 6-membered monocyclic heteroaryl group, and
 (r9) a 5- or 6-membered monocyclic heteroaryl$C_{1-4}$ alkyl group,
(s) a $C_{1-6}$ alkoxy group,
(t) a $C_{6-10}$ aryloxy group,
(u) an oxo group.
(v) a 5- or 6-membered monocyclic heteroaryl group,
(w) a 5- or 6-membered monocyclic heteroarylcarbonyl group,
(x) a 3- to 8-membered saturated heterocyclic group,
(y) a 3- to 8-membered saturated heterocyclic carbonyl group,
(z) an aminocarbonyl group optionally substituted with a group selected from the above-shown (r1) to (r9),
(aa) a 5- or 6-membered monocyclic heteroaryloxy group.
(ab) a 3- to 8-membered saturated heterocyclic oxy group,
(ac) a 3- to 8-membered saturated heterocyclic oxycarbonyl group,
(ad) a $C_{1-6}$ alkylsulfonyl group,
(ae) a $C_{6-10}$ arylsulfonyl group,
(af) a $C_{1-6}$ alkoxycarbonyl group,
(ag) a $C_{3-10}$ cycloalkoxycarbonyl group, and
(ah) a 4- to 7-membered cyclic amino group optionally substituted with a group selected from the above-shown (r1) to (r9).

The terms "an optionally-substituted $C_{2-6}$ alkenyl group", "an optionally-substituted $C_{2-6}$ alkynyl group", "an optionally-substituted $C_{1-6}$ alkylthio group", "an optionally-substituted $C_{1-6}$ alkylsulfinyl group", "an optionally-substituted $C_{1-6}$ alkylsulfonyl group", "an optionally-substituted $C_{1-4}$ alkylcarbonyl group", and "an optionally-substituted $C_{1-6}$ alkoxy group" as used herein mean that they may optionally have one substituent selected from, for example, the above-listed (a) to (ah) in the term "an optionally-substituted $C_{1-6}$ alkyl group".

The terms "an optionally-substituted $C_{3-10}$ cycloalkyl group". "an optionally-substituted $C_{3-10}$ cycloalkenyl group", "an optionally-substituted $C_{3-10}$ cycloalkylsulfinyl group", "an optionally-substituted $C_{3-10}$ cycloalkylsulfonyl group", "an optionally-substituted $C_{3-10}$ cycloalkylcarbonyl group", "an optionally-substituted 3- to 8-membered saturated heterocyclic group", and "an optionally-substituted 3- to 8-membered saturated heterocyclic carbonyl group" as used herein mean that they may optionally have one substituent selected from the group consisting of, for example, the above-listed (a) to (ah) in the term "an optionally-substituted $C_{1-6}$ alkyl group", and a $C_{1-4}$ alkyl group optionally substituted with a carboxy or 4- to 7-membered cyclic amino group.

The terms "an optionally-substituted $C_{6-10}$ aryl group", "an optionally-substituted $C_{6-10}$ arylthio group", "an optionally-substituted $C_{6-10}$ arylsulfinyl group", "an optionally-substituted $C_{6-10}$ arylsulfonyl group", "an optionally-substituted $C_{6-10}$ arylcarbonyl group", "an optionally-substituted 5- to 12-membered monocyclic or polycyclic heteroaryl group", "an optionally-substituted 5- to 12-membered monocyclic or polycyclic heteroarylcarbonyl group", "an optionally-substituted 5- to 12-membered monocyclic or polycyclic heteroarylthio group", "an optionally-substituted 5- to 12-membered monocyclic or polycyclic heteroarylsulfinyl group", and "an optionally-substituted 5- to 12-membered monocyclic or polycyclic heteroarylsulfonyl group" as used herein mean that they may optionally have 1 to 5 substituents selected from the group consisting of, for example, the above-listed (a) to (ah) in the term "an optionally-substituted $C_{1-6}$ alkyl group", a $C_{1-4}$ alkyl group optionally substituted with a carboxy or 4- to 7-membered cyclic amino group, a $C_{2-6}$ alkenyl group, and a $C_{2-6}$ alkynyl group.

The term "an optionally-substituted 4- to 7-membered cyclic amino group" as used herein means that it may optionally have a substituent selected from, for example, the above-listed (r1) to (r9) in the term "an optionally-substituted $C_{1-6}$ alkyl group".

The term "pharmaceutically acceptable salt" as used herein includes an acid addition salt and a base addition salt. For example, the acid addition salt includes inorganic acid salts such as hydrochloride, hydrobromide, sulfate, hydroiodide, nitrate and phosphate; and organic acid salts such as citrate, oxalate, acetate, formate, propionate, benzoate, trifluoroacetate, methanesulfonate, benzenesulfonate, p-toluenesulfonate and camphorsulfonate. The base addition salt includes inorganic base salts such as a sodium salt, a potassium salt, a calcium salt, a magnesium salt and an ammonium salt; and organic base salts such as a triethylammonium salt, a triethanolammonium salt, a pyridinium salt and a diisopropylammonium salt, and also an amino-acid salt (e.g. salts of basic or acidic amino acids such as arginine, aspartic acid and glutamic acid).

In order to obtain a salt of the present compound, a salt form of the present compound may be directly purified, or a free form thereof may be dissolved or suspended in an appropriate organic solvent with the addition of acids or bases to form its salt in a conventional manner.

The present invention includes the compound of Formula (1), and a prodrug and pharmaceutically acceptable salt thereof; and also a solvate thereof such as a hydrate or ethanol solvate thereof. Furthermore, the present invention includes any type of tautomer, stereoisomer and crystal form of the present compound of Formula (1).

The term "prodrug" as used herein refers to a compound which is converted into the compound of Formula (1) by a reaction with an enzyme, gastric acid or the like under a physiological condition in the living body (e.g. enzymatic oxidation, reduction, hydrolysis or the like).

The present compound may have at least one asymmetric carbon atom. Thus, the present invention includes a racemate of the present compound, and also an optically active substance thereof. In case that the present compound has two or more asymmetric carbon atoms, it may exist as stereoisomers. Thus, the present invention also includes stereoisomers of the present compound and mixtures thereof.

Hereinafter, processes of the present compound of Formula (1) are explained with some illustrations, but the present invention should not be limited thereto.

The present compound of Formula (1) can be prepared from a well-known compound by Processes 1 to 8 shown below, processes similar thereto, or processes known to those in the art, which may be used alone or in combination if necessary. In addition, the abbreviations shown below may be optionally used herein for the purpose of simplifying the description.

Boc: tert-butoxycarbonyl group
Cbz: benzyloxycarbonyl group
TMS: trimethylsilyl group
TBS: tert-butyldimethylsilyl group
SEM: 2-[(trimethylsilyl)ethoxy]methyl group
Ac: acetyl group
Me: methyl group
Et: ethyl group
Pr: propyl group
i-Pr: isopropyl group
Bu: butyl group
i-Bu: isobutyl group
t-Bu: tert-butyl group
Ph: phenyl group
Bn: benzyl group
Ms: methanesulfonyl group
TFA: trifluoroacetic acid
Alloc: allyloxycarbonyl group Process 1

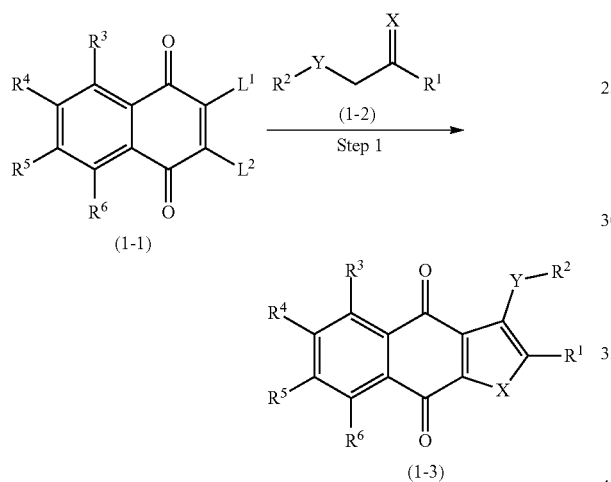

wherein $R^1$, $R^2$, $R^3$, $R^4$, $R^5$, $R^6$, X and Y are as defined above, and $L^1$ and $L^2$ are independently a hydrogen atom, a hydroxy group or a leaving group such as a chlorine atom, a bromine atom, an iodine atom, a methanesulfonyloxy group, a trifluoromethanesulfonyloxy group and a p-toluenesulfonyloxy group.

(Step 1)

Compound (1-1) is reacted with Compound (1-2) in an organic solvent in the presence of a base to give Compound (1-3), wherein Compounds (1-1) and (1-2) can be prepared by well-known processes or processes shown below.

The organic solvent used herein includes aprotic solvents such as N,N-dimethylformamide. N-methyl-2-pyrrolidone and dimethylsulfoxide; ether solvents such as tetrahydrofuran and 1,4-dioxane; halogenated hydrocarbon solvents such as dichloromethane, chloroform, 1,2-dichloroethane and chlorobenzene; hydrocarbon solvents such as toluene and benzene; and mixtures thereof. The organic solvent is preferably N,N-dimethylformamide, N-methylpiperidone, dimethylsulfoxide, acetonitrile, or tetrahydrofuran. The reaction can also be carried out in a two-phase system of the organic solvent and water.

The base used herein includes any type thereof, i.e. both an organic base and an inorganic base. The organic base includes 1-hydroxybenzotriazole, N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylaminopyridine and picoline. The inorganic base includes alkali halides such as potassium fluoride; alkali hydroxides such as sodium hydroxide and potassium hydroxide; sodium bicarbonate; alkali carbonates such as sodium carbonate, potassium carbonate and cesium carbonate; alkali alkoxides such as sodium ethoxide, sodium tert-butoxide and potassium tert-butoxide; and alkali metals such as n-butyllithium, methyl lithium and isopropyl magnesium bromide.

The reaction temperature herein can be selected from the range of about −78° C. to about 200° C. The reaction temperature is typically about −20° C. to about 180° C., preferably about 0° C. to about 150° C.

The amount of Compound (1-2) used herein is typically 1 mol to 5 mol, preferably 1.2 mol to 3 mol per mol of Compound (1-1). The amount of base used herein is typically 2 mol to 10 mol, preferably 2 mol to 3 mol per mol of Compound (1-1).

The reaction time herein is typically about 0.5 to about 48 hours, preferably about 0.5 to about 12 hours.

Process 2

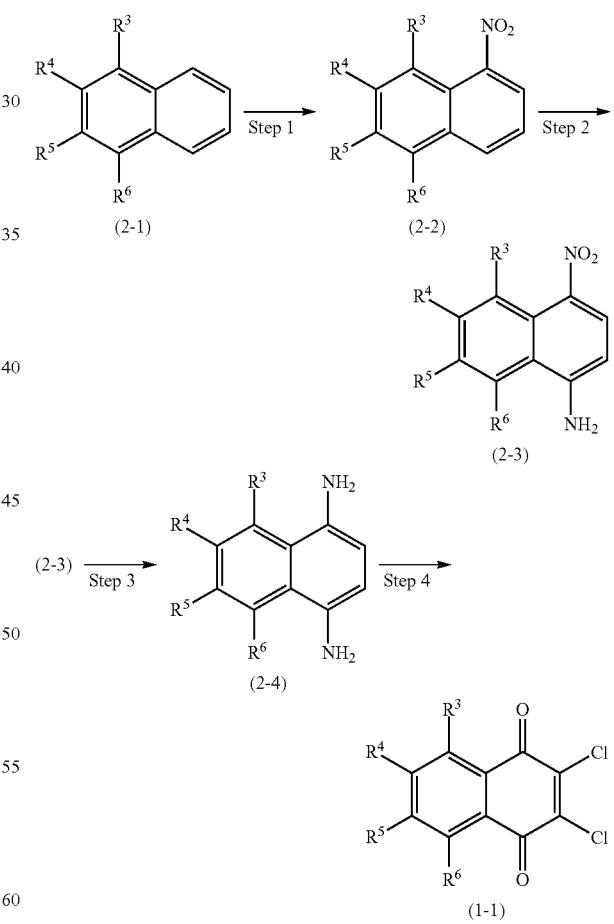

wherein $R^3$, $R^4$, $R^5$ and $R^6$ are as defined above.

Steps 1 to 4 herein can be carried out to prepare Compound (1-1) from Compound (2-1) according to methods similar to those disclosed in documents such as *Bioorganic & Medicinal Chemistry Letters,* 1075, vol. 9, (1999); *Bio-* organic & Medicinal Chemistry Letters, 6001, vol. 16, (2006); Bioorganic & Medicinal Chemistry Letters, 2577, vol. 17, (2007); European Journal of Medicinal Chemistry, 3938, vol. 45, (2010); Tetrahedron Letters, 4119, vol. 21, (1980); and J. Med. Chem. 1329, vol. 29, (1986).

Process 3

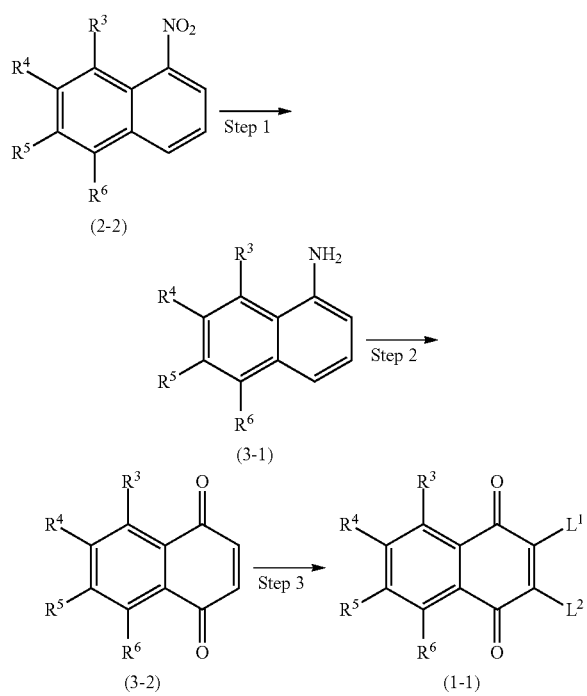

wherein $R^3$, $R^4$, $R^5$ and $R^6$ are as defined above, and $L^1$ and $L^2$ are independently a hydrogen atom, a hydroxy group or a leaving group such as a chlorine atom, a bromine atom and an iodine atom.

Steps 1 to 3 herein can be carried out to prepare Compound (1-1) from Compound (2-2) according to methods similar to those disclosed in documents such as Bioorganic & Medicinal Chemistry Letters, 171, vol. 16, (2006); Bioorganic & Medicinal Chemistry Letters, 4617, vol. 16, (2008); Bioorganic & Medicinal Chemistry Letters, 5924, vol. 19, (2009); US 2006/40996 A1; Tetrahedron Letters, 4119, vol. 21, (1980); Tetrahedron Letters, 6769, vol. 50, (2009); J. Med Chem. 1329 and 1504, vol. 29. (1986); and J. Am. Chem. 2540, vol. 132, (2010).

Process 4

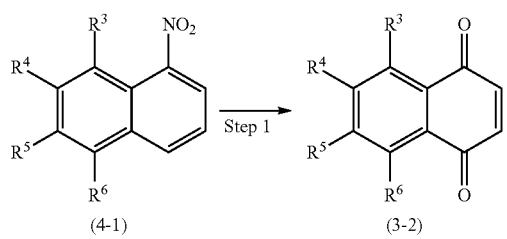

wherein $R^3$, $R^4$, $R^5$ and $R^6$ are as defined above.

The step herein can be carried out to prepare Compound (3-2) from Compound (4-1) according to methods similar to those disclosed in documents such as Bioorganic & Medicinal Chemistry Letters, 127, vol. 17, (2007); Bioorganic & Medicinal Chemistry Letters, 9432, vol. 16, (2008); US 2006/40996 A1; Tetrahedron Letters, 5611, vol. 24, (1983); Tetrahedron Letters, 4329, vol. 42, (2001); J. Med. Chem. 2634, vol. 51, (2008); and Green Chemistry, 318, vol. 11, (2009).

Process 5

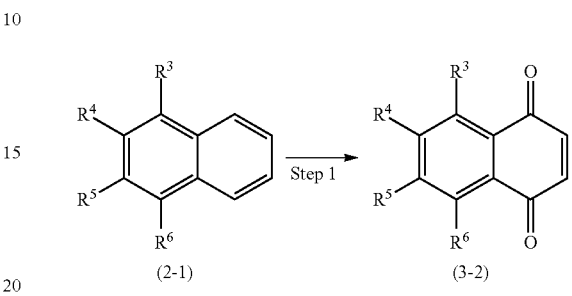

wherein $R^3$, $R^4$, $R^5$ and $R^6$ are as defined above.

The step herein can be carried out to prepare Compound (3-2) from Compound (2-1) according to methods similar to those disclosed in documents such as Tetrahedron, 4997, vol. 40, (1984); Tetrahedron, 9763, vol. 68, (2012); Tetrahedron Letters, 5611, vol. 24, (1983); Tetrahedron Letters, 4329, vol. 42, (2001); J. Med. Chem., 730, vol. 25, (1982); Chemical and Pharmaceutical Bulletin. 4671, vol. 33, (1985); Chemistry—A European Journal, 3899, vol. 11, (2005); WO 2011/66263 A1; and WO 2005/123644 A2.

Process 6

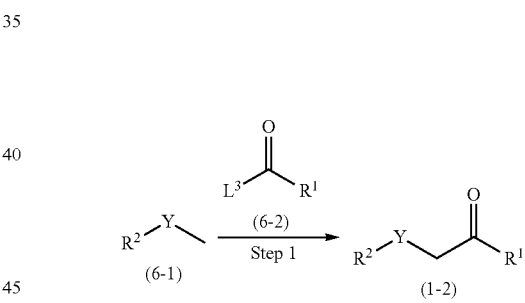

wherein $R^1$, $R^2$ and Y are as defined above, and $L^3$ is a leaving group such as a chlorine atom, a bromine atom, an iodine atom, a methoxy group, an ethoxy group, a propoxy group, and a butoxy group.

The step herein can be carried out to prepare Compound (1-2) from Compound (6-1) according to methods similar to those disclosed in documents such as Bioorganic & Medicinal Chemistry, 5705, vol. 20, (2012); Tetrahedron, 518, vol. 67, (2011); J. Am. Chem., 3460, vol. 103, (1981); J. Am. Chem., 11326, vol. 126, (2004); J. Med. Chem., 1347, vol. 40, (1997); J. Med. Chem., 5233, vol. 45, (2002); Journal of Heterocyclic Chemistry, 815, vol. 27, (1990); WO 2008/124745 A1; WO 2005/000822 A1; US 2013/217918 A1; US 2011/105497 A1; US 2012/220784 A1; and WO 2004/41264 A1.

Process 7

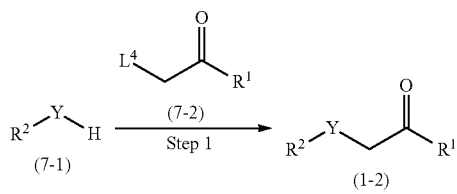

wherein $R^1$, $R^2$ and Y are as defined above, and $L^4$ is a leaving group such as a chlorine atom, a bromine atom, an iodine atom, a methanesulfonyloxy group, a trifluoromethanesulfonyloxy group, a p-toluenesulfonyloxy group and a trimethylamino group.

The step herein can be carried out to prepare Compound (1-2) from Compound (7-1) according to methods similar to those disclosed in documents such as *Bioorganic & Medicinal Chemistry Letters*, 2922, vol. 22, (2012); *J. Med. Chem.*, 2771, vol. 36, (1993); *J. Med. Chem.*, 954, vol. 31, (1988); WO 2009/106817 A2; and U.S. Pat. No. 5,466,827 A1.

Process 8

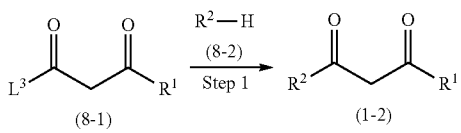

wherein $R^1$ and $R^2$ are as defined above, and $L^3$ is a leaving group such as a chlorine atom, a bromine atom, an iodine atom, a methoxy group, an ethoxy group, a propoxy group, a butoxy group, an imidazole group, a pyrrole group and an optionally-substituted phenoxy group.

The step herein can be carried out to prepare Compound (1-2) from Compound (8-1) according to methods similar to those disclosed in documents such as *Org. Lett.*, 1239, vol. 7, (2002); *Org. Lett.*, 2856, vol. 11, (2009); and US 2013/109662 A1.

In each of the reactions explained in the above processes, there are cases where the use of a protecting group is not clearly disclosed, but a group other than the reactive site is reacted under the reaction conditions or is not suitable to carry out the method. In such cases, if necessary, the group other than the reactive site may be protected and then deprotected after the reaction or after a series of the reactions to give the desired compound. The protecting group used herein includes conventional protecting groups such as those disclosed in *Protective Groups in Organic Synthesis*, 4th ed., T. W. Greene, John Wiley & Sons Inc. (2006). In more specific, the protecting group for the amino group includes benzyloxycarbonyl, tert-butoxycarbonyl, acetyl, benzyl and the like; and the protecting group for the hydroxy group includes trialkylsilyl (e.g. trimethylsilyl and tert-butyldimethylsilyl), acetyl, benzyl and the like. Introduction and deprotection of the protecting group can be carried out according to methods routinely used in synthetic organic chemistry (e.g. see, the above-mentioned *Protective Groups in Organic Synthesis*) or similar methods thereto.

The protecting groups, condensing agents and the like used herein may be optionally indicated by abbreviations commonly used in the technical field, i.e. IUPAC-IUB (International Union of Biochemistry). Preferred salts and pharmaceutically acceptable salts of the starting compounds and the desired compounds are nontoxic salts commonly used, and include acid addition salts such as organic acid salts (e.g. acetate, trifluoroacetate, maleate, fumarate, citrate, tartrate, methanesulfonate, benzenesulfonate, formate, and toluenesulfonate) and inorganic acid salts (e.g. hydrochloride, hydrobromide, hydroiodide, sulfate, nitrate, and phosphate); salts with an amino acid such as arginine, aspartic acid and glutamic acid; metal salts such as alkali metal salts (e.g. sodium and potassium salts) and alkaline earth metal salts (e.g. calcium and magnesium salts); an ammonium salt; organic base salts such as trimethylamine, triethylamine, pyridine, picoline, dicyclohexylamine and N,N'-dibenzylethylenediamine salts); and other salts which can be used by those skilled in the art.

In order to prepare compounds which are included in the present invention but not clearly disclosed in the above processes, the functional groups of the intermediates or final products in the above processes may be optionally modified (in particular, the side chains may be extended variously starting from amino, hydroxy, carbonyl, halogen groups and the like) and if necessary subjected to the above-mentioned protection and deprotection. The modification of functional groups and the extension of side chains can be carried out according to conventional methods [e.g. see, *Comprehensive Organic Transformations*, R. C. Larock, John Wiley & Sons Inc. (1999)].

The intermediates and desired compounds in each of the above processes can be isolated and purified according to purification methods routinely used in synthetic organic chemistry (e.g. neutralization, filtration, extraction, washing, drying, concentration, recrystallization, and various types of chromatography). In addition, some of the intermediates may be directly used in the next reaction without purification.

The present compound of Formula (1) may exist as optical isomers due to an optically-active center, atropisomers which show axial or planar chirality due to restricted rotation in the molecule, other stereoisomers, tautomers, geometric isomers or the like. Thus, the present invention includes all types of possible isomers (including the above-mentioned isomers) and mixtures thereof.

In particular, an optical isomer can be obtained as a racemate; and an atropisomer can be obtained as an optically active substance in case that an optically-active starting material or intermediate is used. If necessary, the racemate of the corresponding staring material, intermediate or final product can be physically or chemically resolved into its optical enantiomers by well-known resolution methods (e.g. using an optically active column and fractional crystallization) at an appropriate stage in the above processes. For example, in case of diastereomer method, two types of diastereomer are obtained from a racemate through a reaction with an optically active resolving agent. The two different diastereomers generally have different physical properties, and thus can be resolved according to well-known methods such as fractionated crystallization.

In order to obtain a pharmaceutically acceptable salt of the present compound of Formula (1), a pharmaceutically acceptable salt form of the present compound may be directly purified, or a free form thereof may be dissolved or suspended in an appropriate organic solvent with the addition of acids or bases to form its salt in a conventional manner. Furthermore, the present compound may exist in the form of an adduct with water or other various solvents, and such adducts are also included in the present invention.

In each of the above-explained processes, there are cases where the processes of the starting compounds and intermediates are not clearly disclosed. In such cases, the starting compounds and intermediates are commercially available, or can be prepared from commercially-available compounds by methods well-known to those skilled in the art or similar methods thereto.

The present compound may be used as, for example, an anticancer agent for any type of cancer including hematological cancer, myeloma, liver cancer, ovarian cancer, prostate cancer, lung cancer, osteosarcoma, colon cancer, breast cancer, skin cancer, epithelial cell cancer (midline carcinoma) and the like. The type of cancer includes preferably hematological cancer, myeloma, liver cancer, ovarian cancer, prostate cancer, lung cancer, osteosarcoma, and colon cancer; and more preferably hematological cancer, prostate cancer, lung cancer, and colon cancer. The term "hematological cancer" as used herein includes lymphoma and leukemia. The present compound can be used as an anticancer agent for the purpose of preventing or treating cancer with the expectation that the present compound can exhibit effects in reducing the size of carcinoma or eliminating carcinoma, or avoiding the increase of carcinoma. In addition, the term "prevent (prevention)" as used herein means that the active ingredient of the present invention is administered to healthy subjects (i.e. those who are not suffering from the disease) for the purpose of, for example, avoiding the onset of the disease. The term "treat (treatment)" as used herein means that the active ingredient of the present invention is administered to patients (i.e. those who are diagnosed as suffering from the disease by a physician) for the purpose of, for example, alleviating the disease or symptom, avoiding the increase of carcinoma, or bringing the patient back to the state before the onset of the disease. In addition, even if the active ingredient of the present invention is administered for the purpose of avoiding the worsening of the disease or symptom, or avoiding the increase of carcinoma, such an administration is also perceived as "treatment" as long as it is administered to patients.

In order to use the present compound for treatment, it can be administered orally or parenterally (e.g. intravenously, subcutaneously, by intramuscular injection, locally, transrectally, percutaneously, and nasally) as a pharmaceutical composition. The formulation for oral administration includes tablets, capsules, pills, granules, powders, liquids, suspensions and the like, which can be formulated according to conventional techniques. In addition, such formulations can comprise nontoxic/inactive carriers or excipients conventionally used in the field of formulation.

The amount of the present compound used for administration may vary depending on factors such as symptom, age and administration method. For example, in case of oral administration, it is desirable that the present compound is administered to an adult human in the range of 0.01 mg (preferably 1 mg) per day as a lower limit and 5000 mg (preferably 500 mg) per day as an upper limit in a single dose or multiple doses, depending on the symptom thereof. In case of intravenous injection, it is expected that the present compound is administered to an adult human in the range of 0.01 mg (preferably 0.1 mg) per day as a lower limit and 1000 mg (preferably 30 mg) per day as an upper limit in a single dose or multiple doses, depending on the symptom thereof, in order to exhibit the efficacy of the present compound.

The present compound can be used in combination with other drugs for the purpose of enhancing the efficacy thereof. In specific, the present compound can be used in combination with a hormone therapy agent, a chemotherapeutic agent, an immunotherapeutic agent, or a pharmacological agent such as a medicament which inhibits cell growth factors and receptor actions thereof. Hereinafter, a drug which can be used in combination with the present compound is abbreviated to "the combined drug".

The hormone therapy agent includes, for example, fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g. tamoxifen citrate and toremifene citrate), pill formulations, mepitiostane, testololactone, aminoglutethimide, LH-RH agonists (e.g. goserelin acetate, buserelin, and leuprorelin), droloxifene, epitiostanol, ethinylestradiol sulfonate, aromatase inhibitors (e.g. fadrozole hydrochloride, anastrozole, letrozole, exemestane, vorozole, and formestane), antiandrogens (e.g. flutamide, bicalutamide, and nilutamide), adrenal corticosteroids (e.g. dexamethasone, prednisolone, betamethasone, and triamcinolone), androgen synthesis inhibitors (e.g. abiraterone), and retinoid and drugs which slow retinoid metabolism (e.g. liarozole).

The chemotherapeutic agent includes, for example, an alkylating agent, an antimetabolite, an anticancer antibiotic, and a plant-derived anticancer agent; and representative examples thereof are listed below.

The alkylating agent includes, for example, nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, dibrospidium hydrochloride, fotemustine, prednimustine, pumitepa, ribomustin, temozolomide, treosulfan, trofosfamide, zinostatin stimalamer, adozelesin, cystemustine, bizelesin, and DDS formulations thereof.

The antimetabolite includes, for example, mercaptopurine, 6-mercaptopurine riboside, thioinosine, methotrexate, pemetrexed, enocitabine, cytarabine, cytarabine ocfosfate, ancitabine hydrochloride, 5-FU type drugs (e.g. fluorouracil, tegafur, UFT, doxifluridine, carmofur, galocitabine, emitefur, and capecitabine), aminopterin, nelzarabine, leucovorin calcium, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine, and DDS formulations thereof.

The anticancer antibiotic includes, for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS formulations thereof.

The plant-derived anticancer agent includes, for example, etoposide, etoposide phosphate, vinblastine sulfate, vincristine sulfate, vindesine sulfate, teniposide, paclitaxel, docetaxel, vinorelbine, and DDS formulations thereof.

The immunotherapeutic agent includes, for example, picibanil, krestin, sizofiran, lentinan, ubenimex, interferon, interleukin, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, PD-1 antibody, and Toll-like Receptor agonists (e.g. TLR7, TLR8, and TLR9 agonists).

The cell growth factor of "a medicament which inhibits cell growth factors and receptor actions thereof" includes any substance as long as it promotes cell growth, and typically factors which are peptides with a molecular weight of 20,000 or less and can exert effects by binding to the receptor at a low concentration. In specific, the cell growth factor includes EGF (epidermal growth factor) or substances which have substantially the same activity (e.g. TGF-alpha), insulin or substances which have substantially the same activity [e.g. IGF (insulin-like growth factor)-1, and IGF-2], FGF (fibroblast growth factor) or substances which have substantially the same activity [e.g. acidic FGF, basic FGF, KGK (keratinocyte growth factor), and FGF-10], and other types of cell growth factors such as CSF (colony stimulating factor), EPO (erythropoietin), IL-2 (interleukin-2), NGF (nerve growth factor), PDGF (platelet-derived growth factor), TGF-beta (transforming growth factor beta), HGF (hepatocyte growth factor), VEGF (vascular endothelial growth factor), heregulin, and angiopoietin.

The interval between administration of the present compound and the combined drug is not limited, and they can be administered to the subjects simultaneously or with a time lag. In addition, the present compound and the combined drug may also be used in the form of a drug combination. The dose of the combined drug can be determined on the basis of the doses used in clinical practice. The mixture ratio of the present compound and the combined drug can be determined on the basis of factors such as the subject, administration route, disease, symptom, and type of the combined drug. For example, in case that the subject is a human, 0.01 to 100 parts by weight of the combined drug may be used per part by weight of the present compound. In addition, the present compound may also be used in combination with an antiemetic drug, a sleep-inducing drug, an anticonvulsant drug and the like for the purpose of reducing side effects.

EXAMPLE

Hereinafter, the present invention is explained in more detail by Reference Examples, Examples and Tests, but the present invention should not be limited thereto.

In addition, note that some of the compound names in Reference Examples and Examples may not follow the IUPAC nomenclature.

Example 1

Methyl 2-(1,1-dimethoxyethyl)-4,9-dioxo-4,9-dihydronaphtho[2,3-b]furan-3-carboxylate

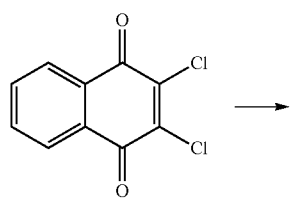

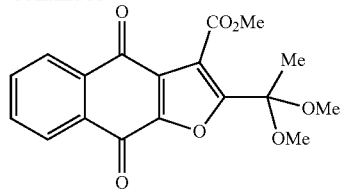

A solution of 2,3-dichloro-1,4-naphthoquinone (2.27 g), methyl 4,4-dimethoxy-3-oxovalerate (2.09 g), and potassium carbonate (3.46 g) in acetonitrile (100 mL) was stirred with heating at 90° C. for 6 hours. The precipitated solid was filtered through Celite with ethyl acetate. The filtrate was concentrated under reduced pressure, and the residue was purified by silica gel column chromatography (ethyl acetate/chloroform) to give the title compound as a yellow solid (2.87 g).

MS (ESI+) 313 (M-OMe$^+$)

Example 2

Methyl 2-acetyl-4,9-dioxo-4,9-dihydronaphtho[2,3-b]furan-3-carboxylate

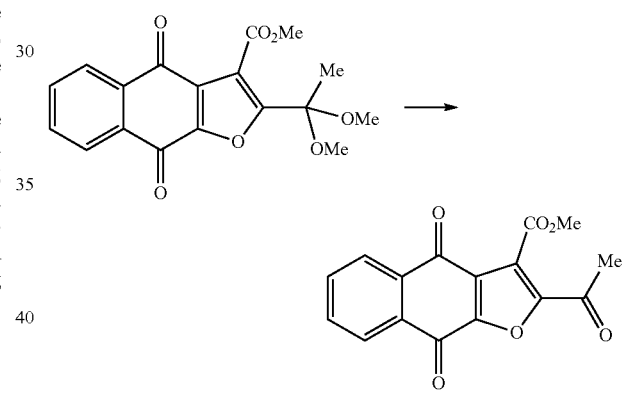

A solution of the compound of Example 1 (1.15 g) in formic acid (20 mL) was stirred at 25° C. for 4 hours. The reaction solution was concentrated under reduced pressure, methanol (10 mL) was added thereto, and the mixture was stirred. The solid was collected on a filter to give the title compound (gray, 0.96 g).

MS (ESI+) 299 (M$^+$+1)

Example 3

2-Acetyl-4,9-dioxo-4,9-dihydronaphtho[2,3-b]furan-3-carboxylic acid

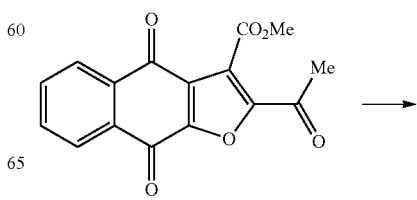

-continued

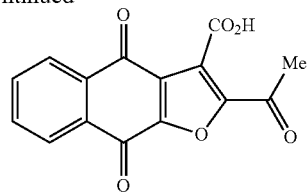

A solution of the compound of Example 2 (0.96 g) in a mixture of 4N HCl/1,4-dioxane (10 mL) and conc. HCl (4 mL) was stirred at 120° C. for 9 hours. The reaction solution was concentrated under reduced pressure. To the residue were added saturated aqueous NaHCO$_3$ solution and ethyl acetate, and the mixture was extracted. The aqueous layer was acidified with HCl, and then extracted with chloroform. The organic layer was washed with brine, dried over Na$_2$SO$_4$, and filtered. The filtrate was concentrated under reduced pressure to give the title compound (gray, 0.44 g).

MS (ESI+) 285 (M$^+$+1)

Example 4

2-Acetyl-N,N-dimethyl-4,9-dioxo-4,9-dihydronaphtho[2,3-b]furan-3-carboxamide

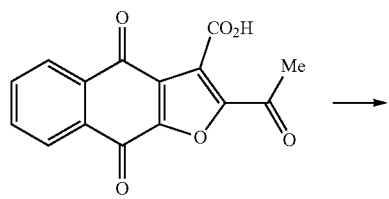

To a solution of the compound of Example 3 (85 mg) and N,N-dimethylformamide (10 mg) in toluene (5 mL) was added dropwise thionyl chloride (143 mg). The reaction solution was stirred with heating at 90° C. for 4 hours, and then concentrated under reduced pressure. To the residue was added tetrahydrofuran (5 mL). To the mixture was added dropwise dimethylamine (2.0 M in tetrahydrofuran, 0.5 mL) at 0° C. The mixture was stirred at 25° C. for 1 hour, and then concentrated under reduced pressure. The residue was purified by silica gel column chromatography (chloroform) to give the title compound as a yellow solid (70 mg).

MS (ESI+) 312 (M$^+$+1)

Example 5

2-Acetyl-3-(4-methylpiperazine-1-carbonyl)naphtho[2,3-b]furan-4,9-dione hydrochloride

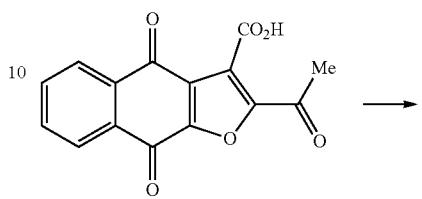

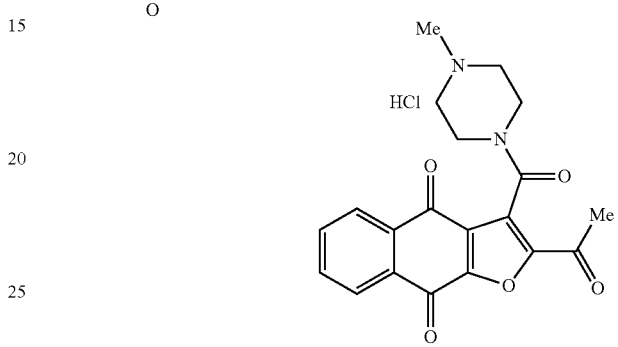

To a solution of the compound of Example 3 (85 mg) and N,N-dimethylformamide (10 mg) in toluene (5 mL) was added dropwise thionyl chloride (143 mg). The reaction solution was stirred with heating at 90° C. for 4 hours, and then concentrated under reduced pressure. To the residue was added tetrahydrofuran (5 mL). To the mixture was added dropwise methylpiperazine (50 mg) at 0° C. The mixture was stirred at 25° C. for 1 hour, and then concentrated under reduced pressure. The residue was purified by silica gel column chromatography (methanol/chloroform) to give a solid. To the solid was added 4N HCl/1,4-dioxane, and the mixture was concentrated to give the title compound as a gray solid (100 mg).

MS (ESI+) 367 (M$^+$+1)

Example 6

Methyl 4,9-dioxo-2-(trifluoromethyl)-4,9-dihydronaphtho[2,3-b]furan-3-carboxylate

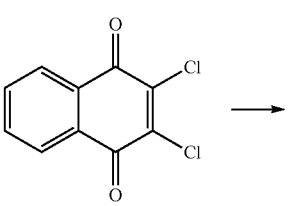

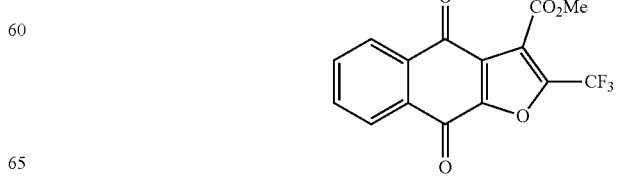

A solution of 2,3-dichloro-1,4-naphthoquinone (2.27 g), methyl-4,4,4-trifluoroacetoacetone (1.87 g) and potassium carbonate (3.46 g) in acetonitrile (100 mL) was stirred with heating at 120° C. for 20 hours. The precipitated solid was filtered through Celite with ethyl acetate. The filtrate was concentrated under reduced pressure, and the residue was purified by silica gel column chromatography (ethyl acetate/chloroform) to give the title compound as a yellow solid (300 mg).

MS (ESI+) 325 (M$^+$+1)

Example 7

4,9-Dioxo-2-(trifluoromethyl)-4,9-dihydronaphtho[2,3-b]furan-3-carboxylic acid

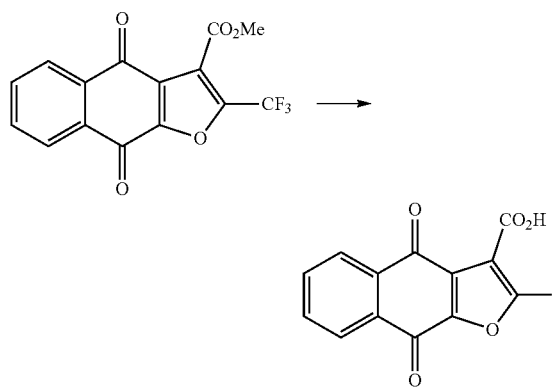

The compound of Example 6 (300 mg) was reacted in the same manner as in Example 3 to give the title compound as a yellow solid (212 mg).

MS (ESI+) 311 (M$^+$+1)

Example 8

3-(4-Methylpiperazine-1-carbonyl)-2-(trifluoromethyl)naphtho[2,3-b]furan-4,9-dione

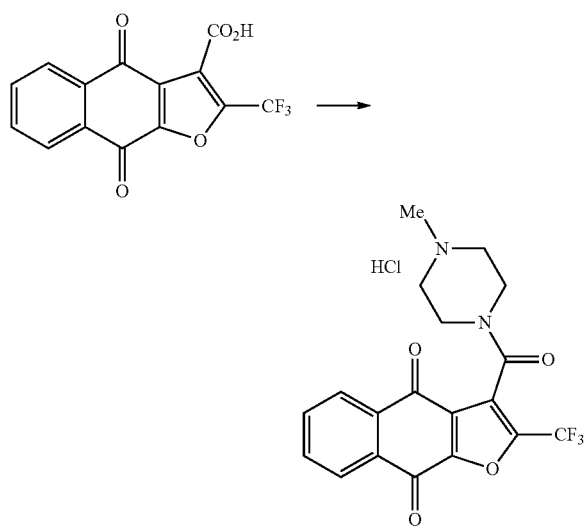

The compound of Example 7 (93 mg) was reacted in the same manner as in Example 5 to give the title compound as an orange solid (84 mg).

MS (ESI+) 393 (M$^+$+1)

Example 9

Methyl 2-(4-fluorophenyl)-4,9-dioxo-4,9-dihydronaphtho[2,3-b]furan-3-carboxylate

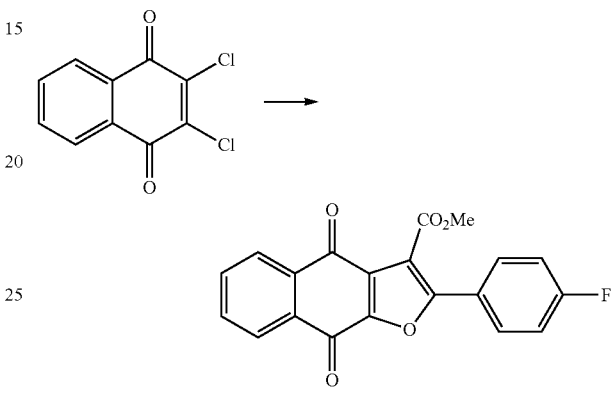

A solution of 2,3-dichloro-1,4-naphthoquinone (227 mg), methyl 3-(4-fluorophenyl)-3-oxopropanoate (200 mg) and potassium carbonate (346 mg) in acetonitrile (10 mL) was stirred with heating at 1100° C. for 6 hours. The mixture was diluted with water. The precipitated solid was collected on a filter to give the title compound as a yellow solid (0.317 mg).

MS (ESI+) 351 (M$^+$+1)

Example 10

2-(4-Fluorophenyl)-4,9-dioxo-4,9-dihydronaphtho[2,3-b]furan-3-carboxylic acid

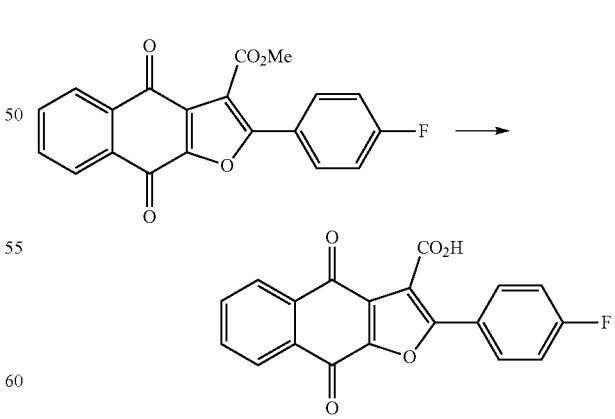

The compound of Example 9 (200 mg) was reacted in the same manner as in Example 3 to give the title compound as a yellow solid (90 mg).

MS (ESI+) 337 (M$^+$+1)

Example 11

2-(4-Fluorophenyl)-N,N-dimethyl-4,9-dioxo-4,9-dihydronaphtho[2,3-b]furan-3-carboxamide

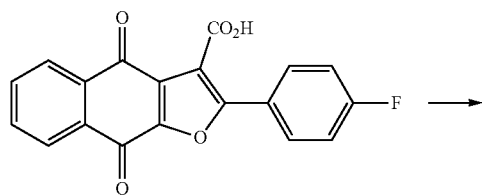

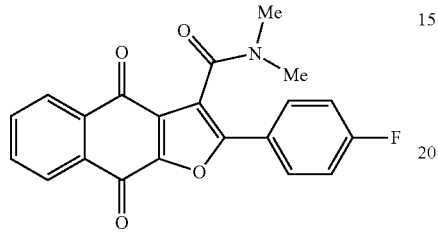

The compound of Example 10 (90 mg) was reacted in the same manner as in Example 4 to give the title compound as a yellow solid (65 mg).
MS (ESI+) 364 (M$^+$+1)

Example 12

Methyl 4,9-dioxo-2-(pyridin-3-yl)-4,9-dihydronaphtho[2,3-b]furan-3-carboxylate

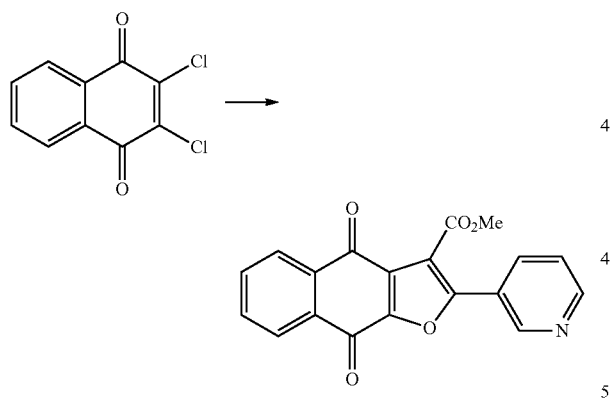

Methyl nicotinoylacetate (188 mg) was reacted in the same manner as in Example 1 to give the title compound as a yellow solid (200 mg).
MS (ESI+) 334 (M$^+$+1)

Reference Example 1

4,4-Dimethoxy-1-morpholinopentane-1,3-dione

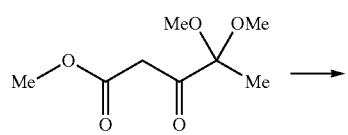

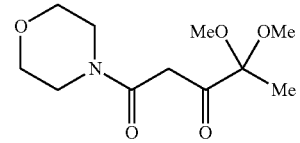

A solution of methyl 4,4-dimethoxy-3-oxovalerate (190 mg), morpholine (480 mg) and DMAP (49 mg) in toluene (2 mL) was stirred with heating at 110° C. for 6 hours. The mixture was cooled to 25° C., and then extracted with ethyl acetate and 1N HCl. The organic layer was washed with brine, dried over $Na_2SO_4$, and filtered. The filtrate was concentrated under reduced pressure to give the title compound as an oil (201 mg).

Example 13

2-(1,1-Dimethoxyethyl)-3-(morpholine-4-carbonyl)naphtho[2,3-b]furan-4,9-dione

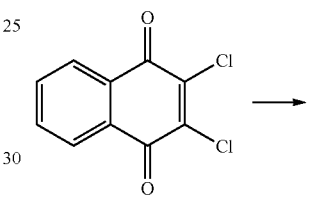

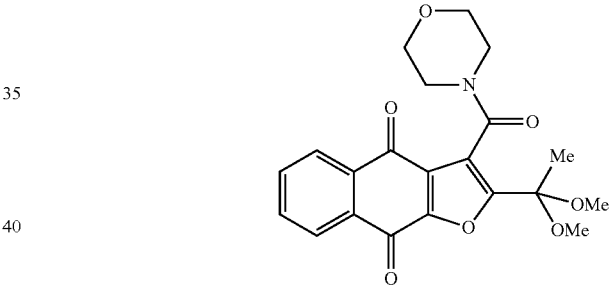

The compound of Reference Example 1 (201 mg) was reacted in the same manner as in Example 1 to give the title compound as a yellow solid (200 mg).
MS (ESI+) 368 (M-OMe$^+$)

Example 14

2-Acetyl-3-(morpholine-4-carbonyl)naphtho[2,3-b]furan-4,9-dione

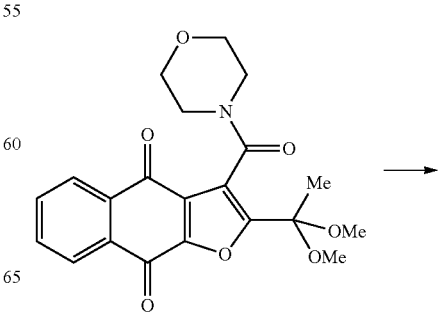

-continued

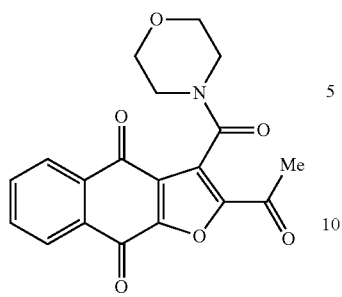

The compound of Example 13 (200 mg) was reacted in the same manner as in Example 2 to give the title compound as a yellow solid (165 mg).

MS (ESI+) 354 (M$^+$+1)

Example 15

Methyl 2-(chloromethyl)-4,9-dioxo-4,9-dihydronaphtho[2,3-b]furan-3-carboxylate

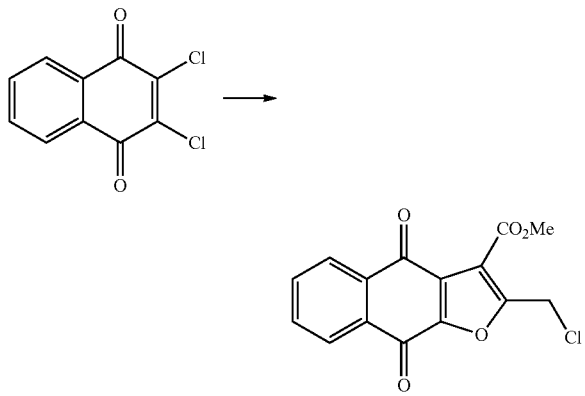

Methyl 4-chloro-3-oxobutanoate (201 mg) was reacted in the same manner as in Example 1 to give the title compound as a yellow solid (48 mg).

MS (ESI+) 305 (M$^+$+1)

Example 16

Methyl 2-(morpholinomethyl)-4,9-dioxo-4,9-dihydronaphtho[2,3-b]furan-3-carboxylate

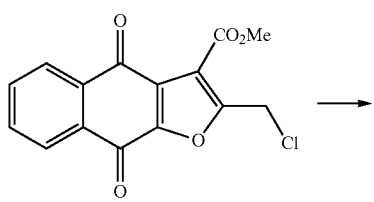

-continued

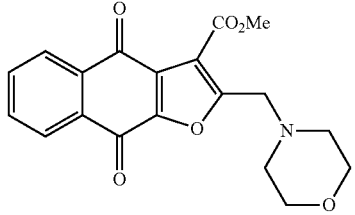

A solution of the compound of Example 15 (48 mg) and morpholine (100 mg) in acetonitrile (2 mL) was stirred at 25° C. for 1 hour. The reaction solution was concentrated under reduced pressure, and the residue was purified by silica gel column chromatography (methanol/chloroform) to give the title compound as a gray oil (40 mg).

MS (ESI+) 356 (M$^+$+1)

Reference Example 2

1-Methyl-4-(methylsulfonyl)piperazine

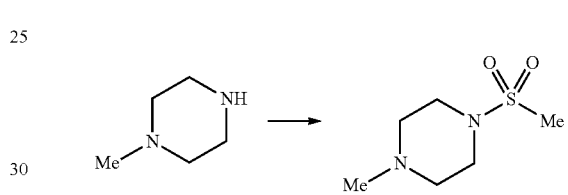

To a solution of 1-methylpiperazine (1.0 g) and triethylamine (2.09 mL) in dichloromethane (70 mL) was added dropwise methanesulfonyl chloride (0.81 mL) at ice temperature, and the mixture was stirred at room temperature for 1 hour. The solvent was evaporated under reduced pressure, and the mixture was partitioned between dichloromethane and 0.5 mol/L aqueous NaOH solution. The organic layer was washed with saturated aqueous NH$_4$Cl solution and brine, and dried over anhydrous Na$_2$SO$_4$. The solvent was evaporated under reduced pressure. To the residue was added hexane, and the precipitated solid was collected on a filter to give the title compound (1.54 g) as a pale-yellow solid.

MS (ESI+) 179 (M$^+$+1)

Reference Example 3

3,3-Dimethoxy-1-((4-methylpiperazin-1-yl)sulfonyl)butan-2-one

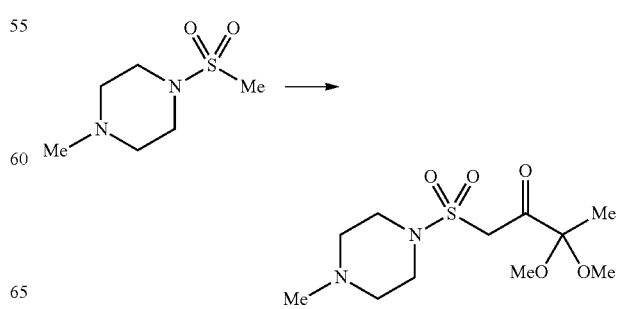

A solution of n-butyllithium in n-hexane (1.58 mol/L, 7.09 mL) was mixed with tetrahydrofuran (18 mL), and the mixture was cooled to −78° C. To the mixture was added dropwise a solution of the compound of Reference Example 2 (1.0 g) in tetrahydrofuran (5 mL), and the mixture was sitted at −78° C. for 1 hour. To the mixture was added dropwise a solution of methyl 2,2-dimethoxypropanoate (0.91 g) in tetrahydrofuran (5 mL), and the mixture was stirred at −78° C. for 1.5 hours. The mixture was heated to room temperature, saturated aqueous NH₄Cl solution was added thereto, and the mixture was extracted with chloroform. The organic layer was washed with brine and dried over anhydrous Na₂SO₄, and the solvent was evaporated under reduced pressure. The residue was purified by silica gel column chromatography (silica gel, chloroform/methanol=98/2-94/6) to give the title compound (1.1 g) as a pale-yellow oil.

MS (ESI+) 295 (M⁺+1)

Example 17

2-(1,1-Dimethoxyethyl)-3-(((4-methylpiperazin-1-yl)sulfonyl)naphtho[2,3-b]furan-4,9-dione

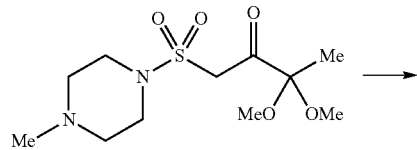

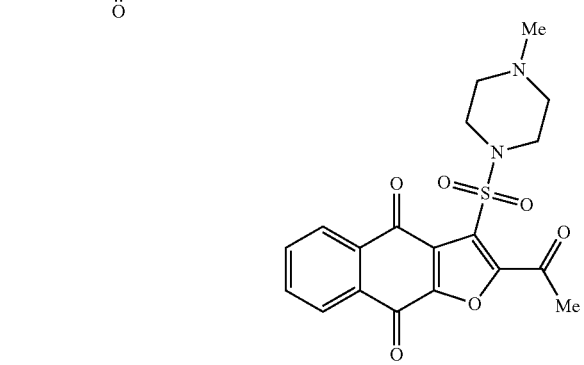

A suspension of the compound of Reference Example 3 (100 mg), 2,3-dichloronaphthalene-1,4-dione (85 mg) and potassium carbonate (117 mg) in acetonitrile (7 mL) was stirred with heating under reflux for 7 hours. The reaction solution was cooled, and partitioned between chloroform and saturated aqueous NH₄Cl solution. The organic layer was washed with brine and dried over anhydrous Na₂SO₄, and the solvent was evaporated under reduced pressure. The residue was purified by silica gel chromatography (silica gel, chloroform/methanol=99/1-95/5) to give the title compound (13 mg) as a red solid.

MS (ESI+) 449 (M⁺+1)

Example 18

2-Acetyl-3-((4-methylpiperazin-1-yl)sulfonyl)naphtho[2,3-b]furan-4,9-dione

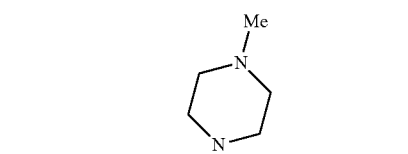

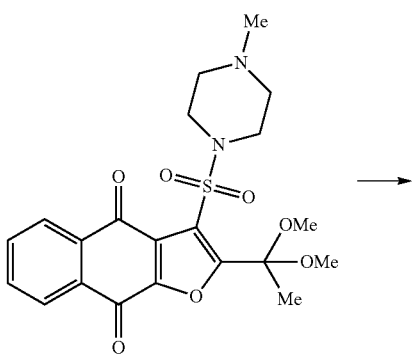

A solution of the compound of Example 17 (10 mg) in formic acid (0.5 mL) was stirred at room temperature for 1 hour. The solvent was evaporated under reduced pressure to give the title compound (9 mg) as a red oil.

MS (ESI+) 403 (M⁺+1)

Reference Example 4

3,3-Dimethoxy-1-(phenylsulfonyl)butan-2-one

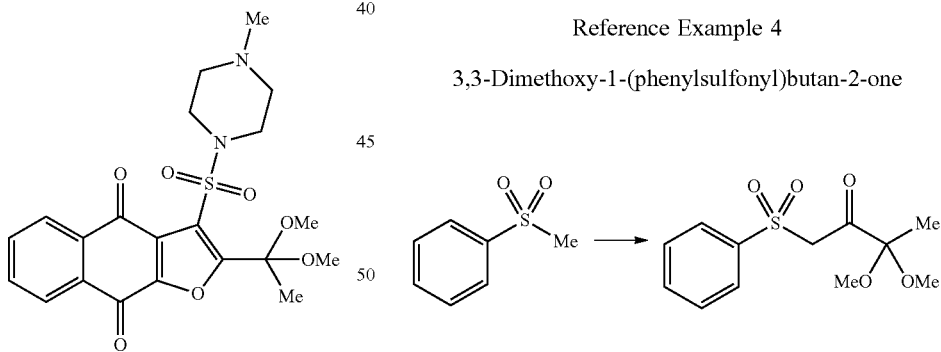

Phenylmethylsulfone (0.50 g) was dissolved in tetrahydrofuran (10 mL), and the solution was cooled to −78° C. To the mixture was added dropwise a solution of n-butyllithium in n-hexane (1.69 mol/L, 2.07 mL), and the mixture was stirred at −78° C. for 30 minutes. To the mixture was added dropwise methyl 2,2-dimethoxypropanoate (0.58 g), and the mixture was stirred at −78° C. for 3.5 hours. The mixture was heated to room temperature, water was added thereto, and the mixture was extracted with ethyl acetate. The organic layer was dried over anhydrous Na₂SO₄, and the solvent was evaporated under reduced pressure. The residue was purified by silica gel column chromatography (hexane/ethyl acetate) to give the title compound (0.86 g) as a colorless oil.

MS (ESI−) 271 (M⁻−1)

Example 19

2-(1,1-Dimethoxyethyl)-3-(phenylsulfonyl)naphtho[2,3-b]furan-4,9-dione

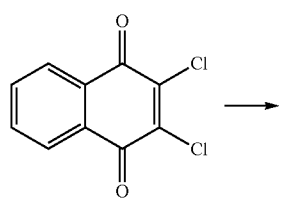

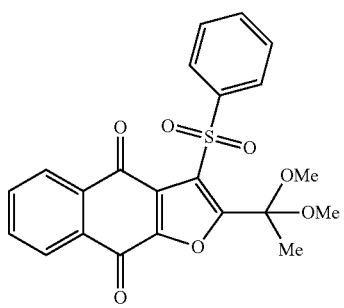

A suspension of the compound of Reference Example 4 (200 mg), 2,3-dichloronaphthalene-1,4-dione (150 mg) and potassium carbonate (230 mg) in acetonitrile (20 mL) was stirred with heating under reflux for 6 hours. The reaction solution was cooled, and partitioned between chloroform and saturated aqueous $NH_4Cl$ solution. The organic layer was dried over anhydrous $Na_2SO_4$, and the solvent was evaporated under reduced pressure. The residue was purified by silica gel column chromatography (chloroform/methanol) to give a solid. The solid was washed with diisopropylether and then collected on a filter to give the title compound (36 mg) as a yellow solid.

MS (ESI+) 395 ($M^+$-OMe)

Example 20

2-Acetyl-3-(phenylsulfonyl)naphtho[2,3-b]furan-4,9-dione

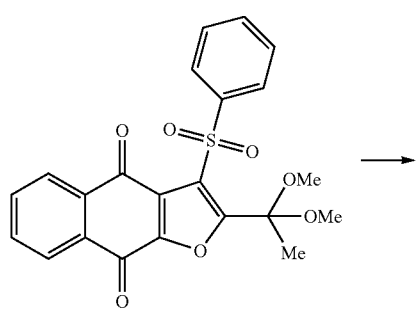

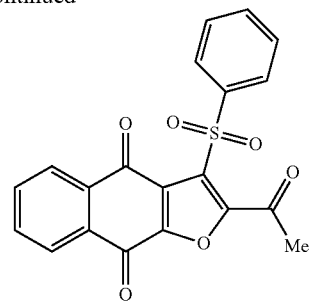

A solution of the compound of Example 19 (36 mg) in formic acid (4 mL) was stirred at room temperature for 1.5 hours. The solvent was evaporated under reduced pressure to give a crude product. The product was washed with diisopropylether and then collected on a filter to give the title compound (34 mg) as a yellow solid.

MS (ESI+) 381 ($M^+$+1)
$^1$H-NMR ($CDCl_3$) δ: 8.52-8.47 (2H, m), 8.24-8.17 (2H, m), 7.85-7.76 (2H, m), 7.69-7.54 (3H, m), 2.79 (3H, s).

Example 21

N,N-dimethyl-4,9-dioxo-2-(trifluoromethyl)-4,9-dihydronaphtho[2,3-b]furan-3-carboxamide

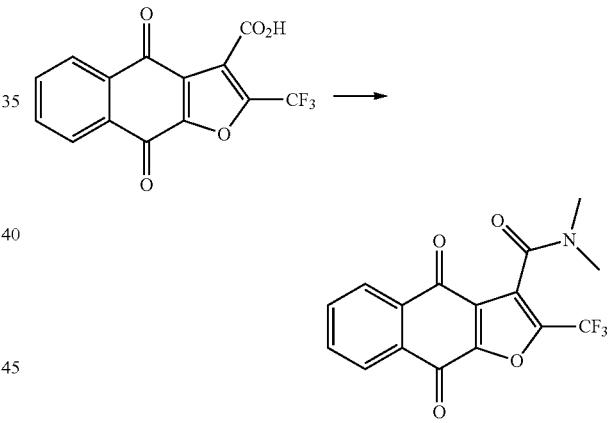

The compound of Example 7 (93 mg) was reacted in the same manner as in Example 4 to give the title compound as a yellow solid (41 mg).

MS (ESI+) 338 ($M^+$+1)

Test 1: Test for Evaluating Growth Inhibition in Cancer Cell

HCT-116 cell, HT-29 cell, and FaDu cell were obtained from the American Type Culture Collection (ATCC). HCT-116 cell and HT-29 cell were cultivated at 37° C. in the presence of 5% $CO_2$ using McCoy's 5a medium containing 10% fetal bovine serum (FBS), and 1% penicillin/streptomycin; and FaDu cell was cultivated at 37° C. in the presence of 5% $CO_2$ using MEM containing 10% FBS, 1% non-essential amino acid, 1% sodium pyruvate, and 1% penicillin/streptomycin. Each cell was seeded on μClear-plate black 384 wells (Greiner bio-one Cat. No. 781091) in 300-600 cells/well, and then each test sample was added thereto to adjust the final concentration thereof in DMSO to 0.1% and the test wells were incubated for 4 days. And then, the viable cell count of each sample was measured using CellTiter-Glo® Luminescent Cell Viability Assay (Promega), and the concentration to inhibit the cell growth in each test sample by 50% was calculated (Bulk $IC_{50}$ Value; μM).

TABLE 1

| Example | $IC_{50}$ (μM) | | |
|---|---|---|---|
| | HCT | FaDu | HT |
| 1 | 0.44 | 0.38 | 2.25 |
| 2 | 0.28 | 0.32 | 0.34 |
| 4 | 0.59 | 0.56 | 0.71 |
| 5 | 0.62 | 0.54 | 0.57 |
| 6 | 2.35 | 2.61 | 2.84 |
| 8 | 0.53 | 0.50 | 0.64 |
| 11 | 5.31 | 4.47 | 5.76 |
| 12 | 6.96 | 2.34 | >10 |
| 14 | 0.74 | 0.75 | 3.58 |
| 21 | 0.27 | 0.30 | 0.30 |

Test 2: Test for Evaluating the Inhibition of Forming Cancer Cell Sphere

HCT-116 cell, HT-29 cell, and FaDu cell were obtained from the American Type Culture Collection (ATCC). HCT-116 cell and HT-29 cell were cultivated at 37° C. in the presence of 5% $CO_2$ using McCoy's 5a medium containing 10% fetal bovine serum (FBS), and 1% penicillin/streptomycin; and FaDu cell was cultivated at 37° C. in the presence of 5% $CO_2$ using MEM containing 10% FBS, 1% non-essential amino acid, 1% sodium pyruvate, and 1% penicillin/streptomycin. Each of HCT-116 cell, HT-29 cell, and FaDu cell was seeded on 384 Wells Black Clear Bottom Ultra-Low Attachment Microplate (Corning Cat. No. 3827) in 350-800 cells/well, with DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penicillin/streptomycin. Each test sample was added thereto to adjust the final concentration thereof in DMSO to 0.1% and the test wells were incubated for 4 days. And then, the viable cell count of each sample was measured using Cell-Titer-Glo® Luminescent Cell Viability Assay (Promega), and the concentration to inhibit the cell growth in each test sample by 50% was calculated (Sphere $IC_{50}$ Value; μM).

TABLE 2

| Example | $IC_{50}$ (μM) | | |
|---|---|---|---|
| | HCT | FaDu | HT |
| 1 | 1.73 | 2.15 | 2.18 |
| 2 | 0.38 | 0.59 | 0.40 |
| 4 | 3.36 | 0.71 | 0.85 |
| 5 | 3.10 | 0.66 | 0.60 |
| 6 | 2.83 | 3.63 | 3.05 |
| 8 | 0.53 | 0.50 | 0.64 |
| 11 | 5.43 | 4.46 | 5.84 |
| 12 | >10 | 5.79 | >10 |
| 14 | 1.80 | 0.54 | 0.71 |
| 21 | 0.32 | 0.41 | 0.32 |

Test 3: Solubility Test

Each 15 μL of each test sample (10 mM DMSO solution) was dispensed into 4 Utubes on a 96 well rack. Then, each sample was evaporated to dryness with a rotary evaporator. 3 μL of DMSO was added to each dried sample to be re-dissolved. And, 300 μL of pH 7.4 buffer was added to the 2 wells and 300 μL of pH 1.2 buffer was added to the other 2 wells. After shaking each sample solution, the samples were still stood. Then, each sample solution was centrifuged to remove insoluble matter, and 100 μL of the supernatant was picked up on a 96 well plate. Separately, 2 μL of each test sample (10 mM DMSO solution) was dispensed on a 96 well plate, and diluted with 198 μL of 50% acetonitrile to prepare each 100 μM standard solution. Further, the 100 μM standard solution was diluted with 50% acetonitrile to prepare each 10 μM standard solution. The above test samples for the solubility test and the two kinds of the standard samples were analyzed with a HPLC. The solubility of each test sample was calculated as an area ratio per the standard solutions.

TABLE 3

| Example | Solubility (mg/mL) | |
|---|---|---|
| | pH 1.2 | pH 7.4 |
| 1 | <0.0003 | <0.0001 |
| 2 | 0.0008 | 0.0005 |
| 4 | 0.115 | 0.107 |
| 5 | 0.152 | 0.127 |
| 6 | 0.0001 | <0.0001 |
| 8 | 0.16 | 0.138 |
| 11 | <0.0001 | <0.0001 |
| 12 | 0.037 | 0.0001 |
| 14 | 0.131 | 0.121 |
| 21 | 0.063 | 0.038 |

Test 4: Concentration of the Test Compounds in Plasma (Measure of the Concentration in Plasma and in Tumor)

Administration method: The test compound scaled to a given weight was suspended in 0.5% methylcellulose to prepare an administration solution. A mouse was weighed, and the administration solution was orally administered to the mouse depending on its weight.

Blood sampling method: EDAT-2K was added to a blood collection tube, into which the blood of the mouse was sampled. The sampled blood was centrifuged to give plasma.

Preparation of standard solution: The test compound scaled to 1 mg was dissolved in 10 mL of MeOH in a volumetric flask to prepare a 100 μg/mL standard solution.

Measure of the concentration in plasma: The 100 μg/mL standard solution was diluted with MeOH to prepare a sample for calibration curve which has the desired concentration. To 50 μL of the sample for calibration curve was added 50 μL of the blank plasma to prepare a sample for plasma calibration curve. To 50 μL of the plasma sample treated with the test compound was added 50 μL of MeOH to prepare a sample for analyzing plasma. To each 100 μL of the sample for plasma calibration curve and the sample for analyzing plasma was added 150 μL of MeOH containing an internal standard respectively. The internal standard used herein was bezafibrate, the concentration of which was 200 nM. Each 5 μL of the samples was analyzed with an LC-MS. The calibration curve was prepared based on the peak ratio of MS peak area of the test sample per that of the internal standard, and the concentration of the sample for plasma calibration curve. The concentration of the test compound in each sample was calculated based on the peak ratio of each sample, and the calibration curve. The compound exposure of Example 8 in plasma and tumor was beyond the IC$_{50}$ values in Tests 1 and 2, hence the compound was thought to be hopeful.

TABLE 4

| Plasma | Concentration of Example 8 (ng/mL) | | | | |
|---|---|---|---|---|---|
| 25 mg/kg po | 1 | 2 | 3 | mean | S.D. |
| 2 hr | 508 | 473 | 384 | 455 | 64 |
| 6 hr | 351 | 2800 | 334 | 1162 | 1419 |

Test 5: Concentration of the Test Compounds in Tumor

The picked tumor was put into a tube, and 1 mL of MeOH containing an internal standard was added to the tube. The internal standard used herein was bezafibrate, the concentration of which was 200 nM. The mixture was homogenized with an electric homogenizer to prepare a tumor extract. And, a blank tumor extract was prepared with a tumor derived from an un-treated animal in the same manner. The 100 μg/mL standard solution was diluted with MeOH to prepare a sample for calibration curve which has the desired concentration. To 50 μL of the sample for calibration curve was added 50 μL of the blank tumor extract to prepare a sample for tumor calibration curve. To 50 μL of the tumor extract was added 50 μL of MeOH to prepare a sample for analyzing tumor. Each 5 μL of the samples was analyzed with an LC-MS. The calibration curve was prepared based on the peak ratio of MS peak area of the test sample per that of the internal standard, and the concentration of the sample for tumor calibration curve. The concentration/weight of the test compound in each sample was calculated based on the peak ratio of each sample, and the calibration curve. Then, the obtained weight was divided by the weight in tumor to calculate the concentration of the test compound in tumor.

TABLE 5

| Tumor | Concentration of Example 8 (ng/mL) | | | | |
|---|---|---|---|---|---|
| 25 mg/kg po | 1 | 2 | 3 | mean | S.D. |
| 2 hr | 498 | 260 | 47 | 268 | 226 |
| 6 hr | 329 | 157 | | | |

INDUSTRIAL APPLICABILITY

The present compound exhibits excellent effects in suppressing the proliferation and sphere-forming ability of cancer cells, and can be preferably used as an antitumor drug or cell growth inhibitor. Furthermore, the present compound can be used for preventing or treating diseases or conditions which may be related to proliferation of cells (e.g. cancer).

The invention claimed is:
1. A compound of Formula (1):

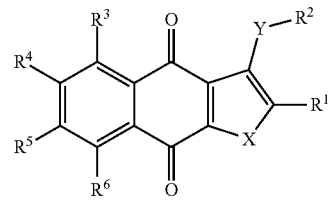

or a pharmaceutically acceptable salt thereof
wherein
X is NR$^7$; Y is —CO—, —CS—, —SO—, or —SO$_2$—;
R$^1$ is a hydrogen atom, a halogen atom, a cyano group, a nitro group, an optionally-substituted C$_{1-6}$ alkoxy group, a substituted amino group, an optionally-substituted C$_{1-6}$ alkylcarbonyl group, an optionally-substituted C$_{3-10}$ cycloalkyl group, an optionally-substituted C$_{3-10}$ cycloalkylcarbonyl group, an optionally-substituted 3- to 8-membered saturated heterocyclic group, an optionally-substituted 3- to 8-membered saturated heterocyclic carbonyl group, an optionally-substituted C$_{6-10}$ arylcarbonyl group, an optionally-substituted 5- to 12-membered monocyclic or polycyclic heteroaryl group, or an optionally-substituted 5- to 12-membered monocyclic or polycyclic heteroarylcarbonyl group;
R$^2$ is a hydrogen atom, a hydroxy group, an optionally-substituted C$_{1-6}$ alkyl group, an optionally-substituted C$_{1-6}$ alkoxy group, an optionally-substituted amino group, an optionally-substituted C$_{3-10}$ cycloalkyl group, an optionally-substituted 3- to 8-membered saturated heterocyclic group, or an optionally-substituted 5- to 12-membered monocyclic or polycyclic heteroaryl group;
R$^3$, R$^4$, R$^5$, and R$^6$ are independently a hydrogen atom, a halogen atom, a cyano group, a nitro group, a hydroxy group, an optionally-substituted C$_{1-6}$ alkyl group, an optionally-substituted C$_{2-6}$ alkenyl group, an optionally-substituted C$_{2-6}$ alkynyl group, an optionally-substituted C$_{1-6}$ alkoxy group, an optionally-substituted C$_{1-6}$ alkylthio group, an optionally-substituted C$_{6-10}$ arylthio group, an optionally-substituted 5- to 12-membered monocyclic or polycyclic heteroarylthio group, an optionally-substituted C$_{1-6}$ alkylsulfinyl group, an optionally-substituted C$_{6-10}$ arylsulfinyl group, an optionally-substituted 5- to 12-membered monocyclic or polycyclic heteroarylsulfinyl group, an optionally-substituted C$_{1-6}$ alkylsulfonyl group, an optionally-substituted C$_{6-10}$ arylsulfonyl group, an optionally-substituted 5- to 12-membered monocyclic or polycyclic heteroarylsulfonyl group, an optionally-substituted amino group, an optionally-substituted C$_{1-6}$ alkylcarbonyl group, an optionally-substituted C$_{3-10}$ cycloalkyl group, an optionally-substituted C$_{3-10}$ cycloalkenyl group, an optionally-substituted 3- to 8-membered saturated heterocyclic group, an optionally-substituted C$_{6-10}$ aryl group, an optionally-substituted 5- to 12-membered monocyclic or polycyclic heteroaryl group, a C$_{1-6}$ alkylsulfinyl group, an optionally-substituted C$_{3-10}$ cycloalkylsulfinyl group, an optionally-substituted $C_{1-6}$ alkylsulfonyl group, or an optionally-substituted $C_{3-10}$ cycloalkylsulfonyl group; and $R^7$ is an optionally-substituted $C_{1-6}$ alkylcarbonyl group, an optionally-substituted $C_{3-10}$ cycloalkyl group, an optionally-substituted 3- to 8-membered saturated heterocyclic group, or an optionally-substituted 5- to 12-membered monocyclic or polycyclic heteroaryl group.

\* \* \* \* \*